(12) United States Patent
Zhang et al.

(10) Patent No.: US 10,646,223 B2
(45) Date of Patent: May 12, 2020

(54) UNIVERSAL HANDLE FOR SURGICAL INSTRUMENTS

(71) Applicant: Covidien LP, Mansfield, MA (US)

(72) Inventors: Xiliang Zhang, Shanghai (CN); Zhaokai Wang, Shanghai (CN)

(73) Assignee: Covidien LP, Mansfield, MA (US)

( * ) Notice: Subject to any disclaimer, the term of this patent is extended or adjusted under 35 U.S.C. 154(b) by 233 days.

(21) Appl. No.: 15/550,831

(22) PCT Filed: Feb. 15, 2015

(86) PCT No.: PCT/CN2015/073116
§ 371 (c)(1),
(2) Date: Aug. 14, 2017

(87) PCT Pub. No.: WO2016/127434
PCT Pub. Date: Aug. 18, 2016

(65) Prior Publication Data
US 2018/0021041 A1   Jan. 25, 2018

(51) Int. Cl.
*A61B 17/072* (2006.01)
*A61B 17/115* (2006.01)
(Continued)

(52) U.S. Cl.
CPC .... *A61B 17/07207* (2013.01); *A61B 17/1155* (2013.01); *A61B 2017/00464* (2013.01);
(Continued)

(58) Field of Classification Search
CPC .. A61B 2017/00477; A61B 2017/2916; A61B 2017/00464; A61B 2017/2923;
(Continued)

(56) References Cited

U.S. PATENT DOCUMENTS 5,799,857 A   9/1998 Robertson et al.
5,865,361 A * 2/1999 Milliman ......... A61B 17/07207
                                                    227/176.1
(Continued)

FOREIGN PATENT DOCUMENTS

CN         1757384 A      4/2006
CN       101530340 A      9/2009
(Continued)

OTHER PUBLICATIONS

European Search Report dated Jan. 31, 2019, issued in EP Appln. No. 15881596.
(Continued)

*Primary Examiner* — Hemant Desai
*Assistant Examiner* — Jacob A Smith
(74) *Attorney, Agent, or Firm* — Carter, DeLuca & Farrell LLP

(57) ABSTRACT

A universal surgical handle (10) includes a body (12) having a moveable handle (18), and elongate member (13) extending distally from the body (12), an actuation shaft (20), and a fire lock mechanism (60). The actuation shaft (20) defines first and second lock slots (24, 25) spaced axially apart. The moveable handle (18) is operatively associated with the actuation shaft (20) to effect longitudinal movement of the actuation shaft (20). The fire lock mechanism (60) has a lock pawl (62) that is received within the first lock slot (24) during a first mode of operation of the handle (10) to lock the actuation shaft (20) in first longitudinal position and is received within the second lock slot (25) during a second mode of operation of the handle (10) to lock the actuation shaft (20) in a second longitudinal position. The handle (10) is adapted to transition from a home position to the first or second mode of operation in response to a loading unit (110, 210) being coupled to the elongate member (13).

19 Claims, 16 Drawing Sheets

(51) Int. Cl.
*A61B 17/00* (2006.01)
*A61B 17/29* (2006.01)
*A61B 90/00* (2016.01)

(52) U.S. Cl.
CPC ........... *A61B 2017/00477* (2013.01); *A61B 2017/2923* (2013.01); *A61B 2090/034* (2016.02)

(58) Field of Classification Search
CPC .. A61B 2017/2913; A61B 2017/07214; A61B 2017/2902; A61B 17/068; A61B 17/2923; A61B 17/072
USPC ..................................................... 227/177.1
See application file for complete search history.

(56) References Cited

U.S. PATENT DOCUMENTS

| | | | |
|---|---|---|---|
| 5,915,616 A | 6/1999 | Viola et al. | |
| 5,964,394 A | 10/1999 | Robertson | |
| 6,032,849 A | 3/2000 | Mastri et al. | |
| 6,045,560 A | 4/2000 | McKean et al. | |
| 6,330,965 B1 | 12/2001 | Milliman et al. | |
| 7,967,178 B2 | 6/2011 | Scirica et al. | |
| 8,453,912 B2* | 6/2013 | Mastri | A61B 17/07207 227/176.1 |
| 2004/0232201 A1* | 11/2004 | Wenchell | A61B 17/068 227/176.1 |
| 2004/0249410 A1 | 12/2004 | Dausch et al. | |
| 2005/0165443 A1* | 7/2005 | Livneh | A61B 18/1445 606/205 |
| 2007/0084898 A1* | 4/2007 | Scirica | A61B 17/0684 227/176.1 |
| 2007/0270884 A1* | 11/2007 | Smith | A61B 17/1114 606/139 |
| 2008/0294192 A1* | 11/2008 | Stefan | A61B 17/1608 606/205 |
| 2008/0314958 A1* | 12/2008 | Scirica | A61B 17/07207 227/175.2 |
| 2009/0145947 A1* | 6/2009 | Scirica | A61B 17/07207 227/175.2 |
| 2009/0206130 A1* | 8/2009 | Hall | A61B 17/07207 227/175.2 |
| 2013/0190732 A1* | 7/2013 | Slisz | A61B 17/1285 606/1 |
| 2013/0248575 A1 | 9/2013 | Marczyk | |
| 2014/0001232 A1 | 1/2014 | Cappola et al. | |
| 2014/0367448 A1* | 12/2014 | Cappola | A61B 17/29 227/177.1 |

FOREIGN PATENT DOCUMENTS

| | | |
|---|---|---|
| CN | 203089257 U | 7/2013 |
| EP | 2722010 A1 | 4/2014 |

OTHER PUBLICATIONS

Chinese Office Action dated Sep. 29, 2019, issued in CN Appln. No. 201580076129. (translation not available).
International Search Report for PCT/CN2015/073116 date of completion is Oct. 30, 2015 (5 pages).

* cited by examiner

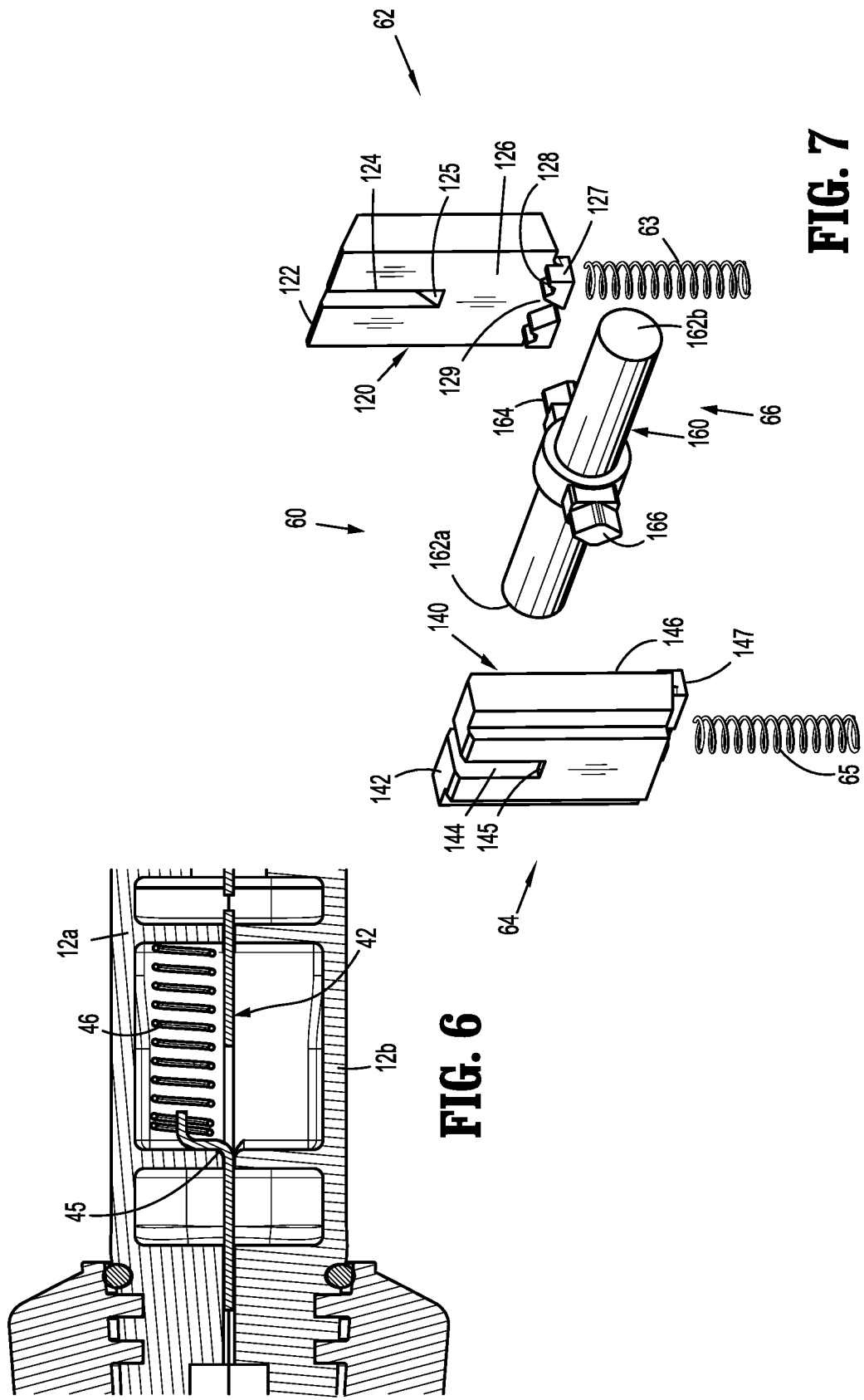

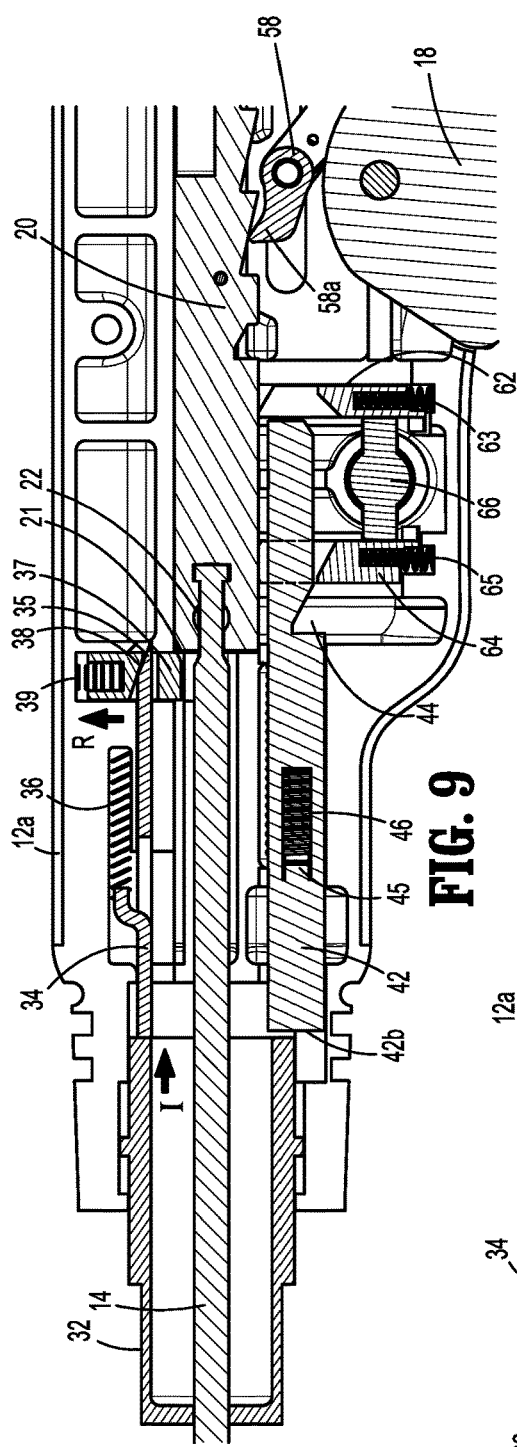
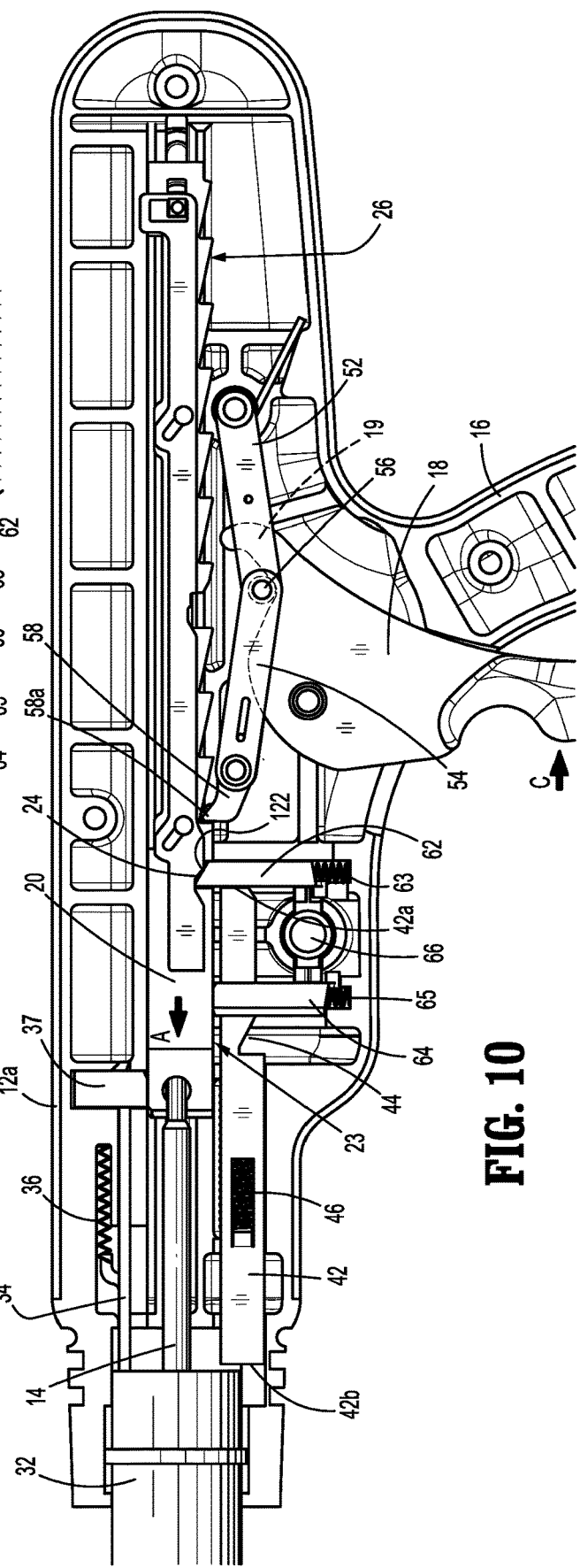
FIG. 9
FIG. 10

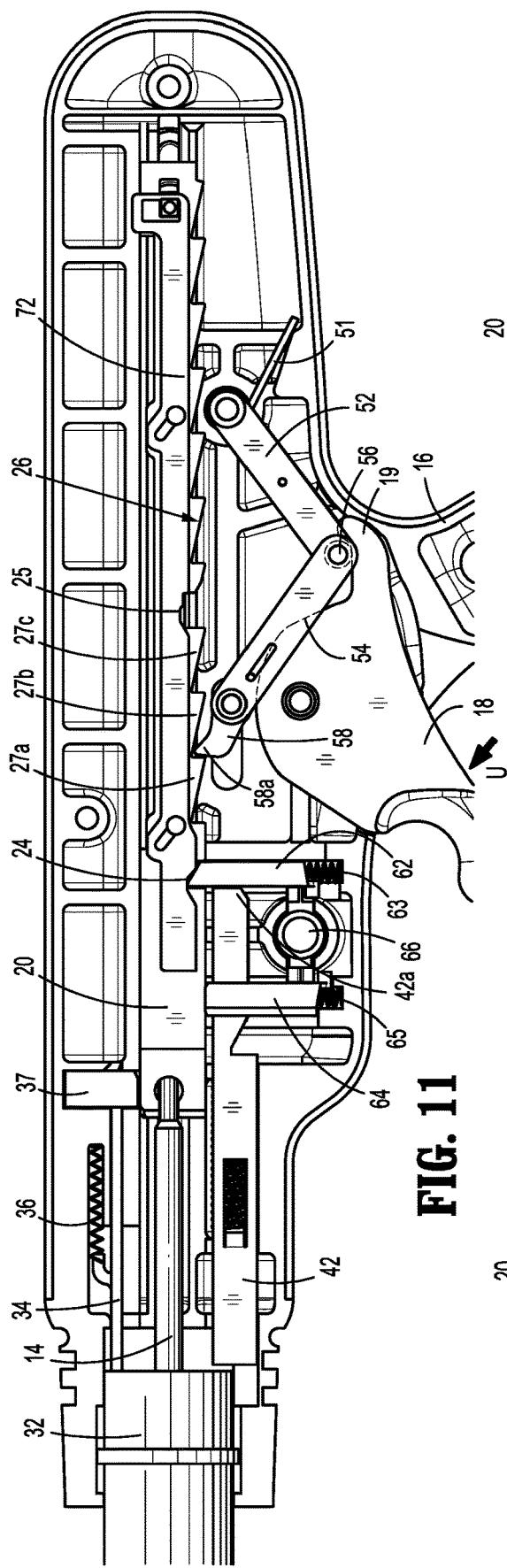
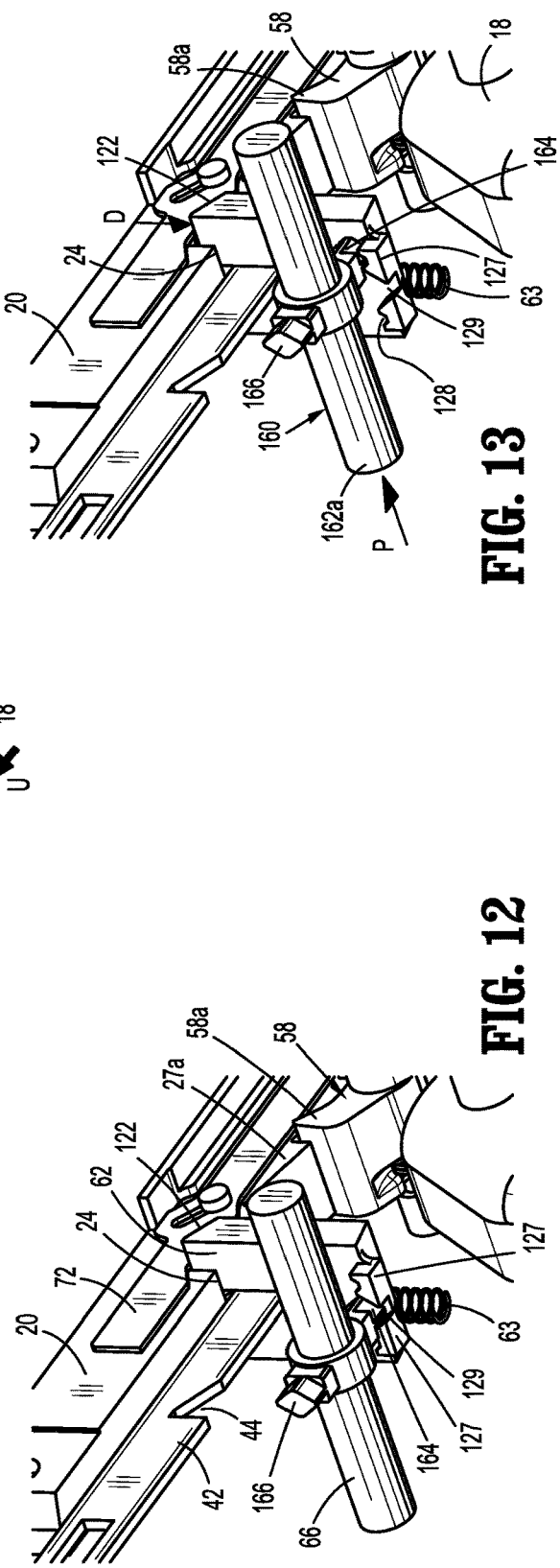
FIG. 11
FIG. 12
FIG. 13

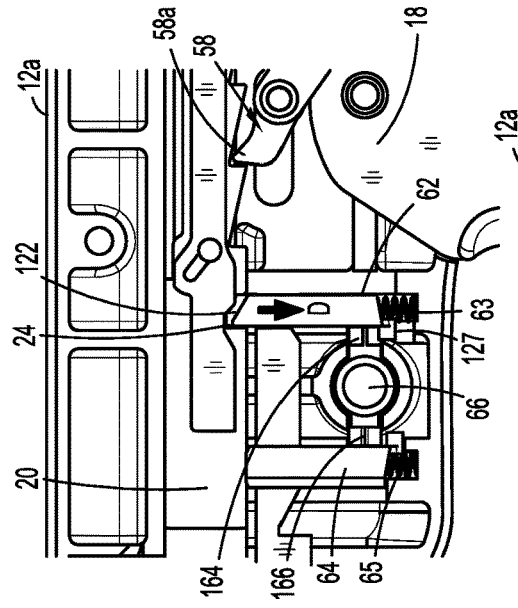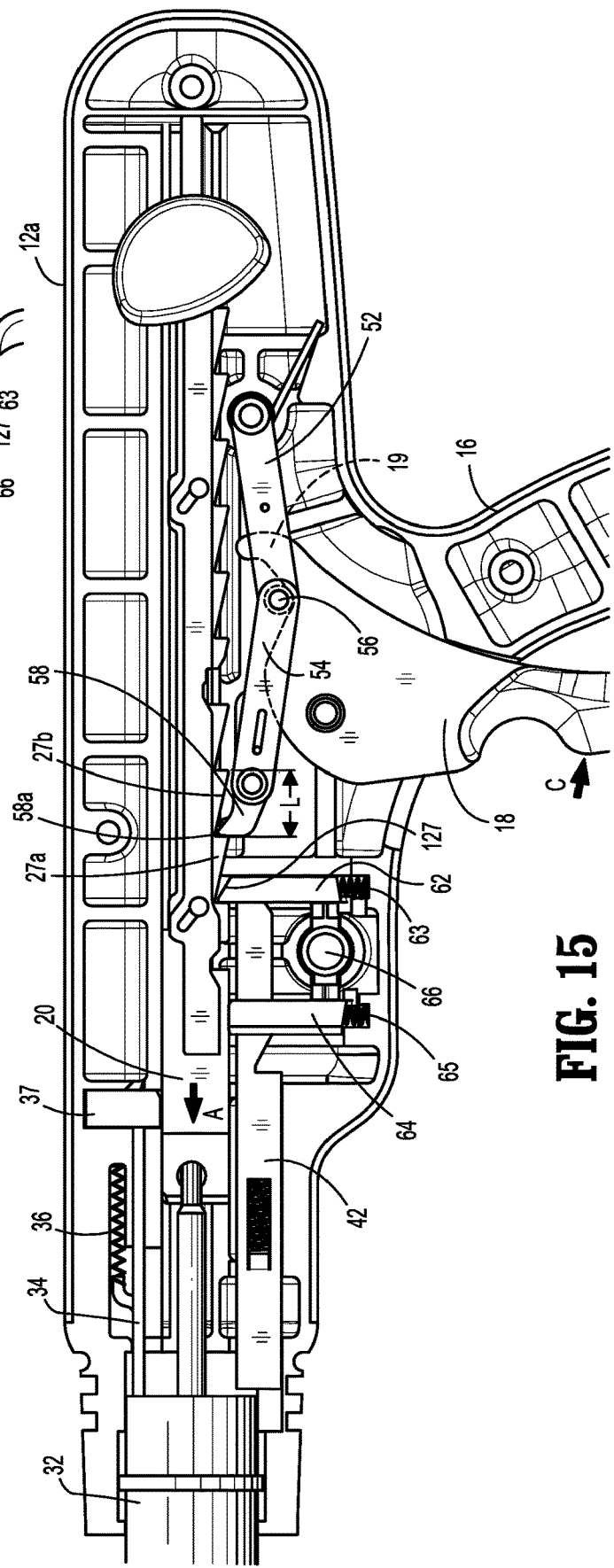

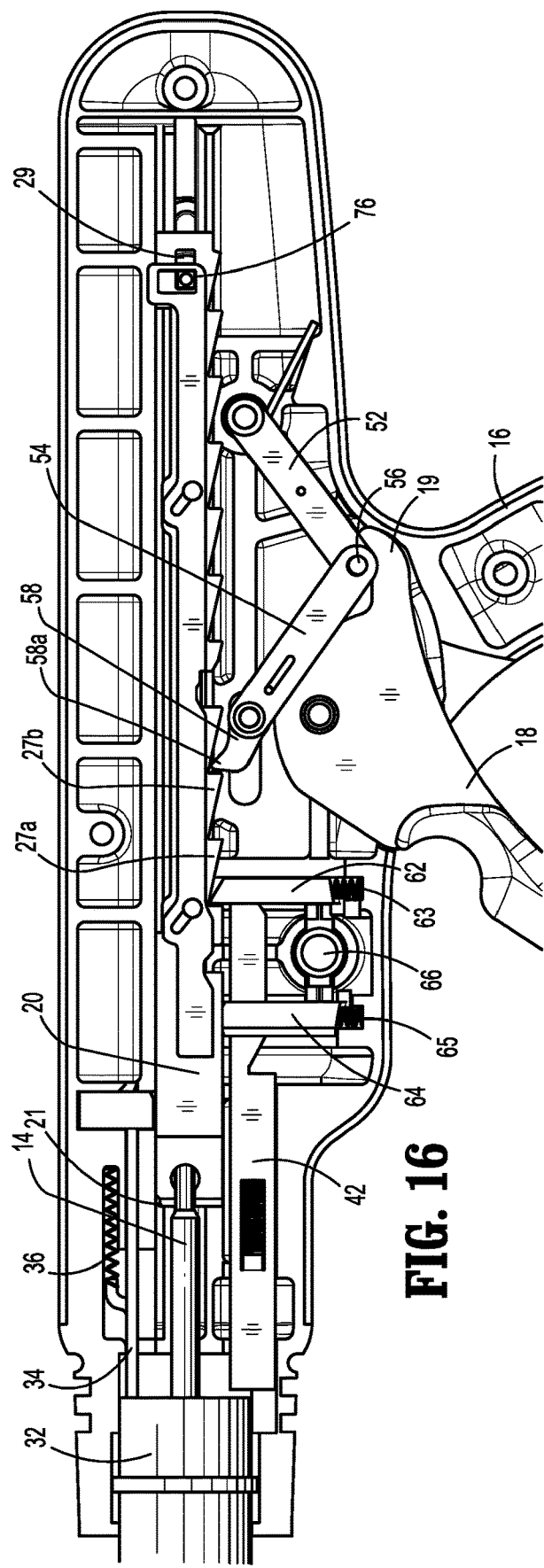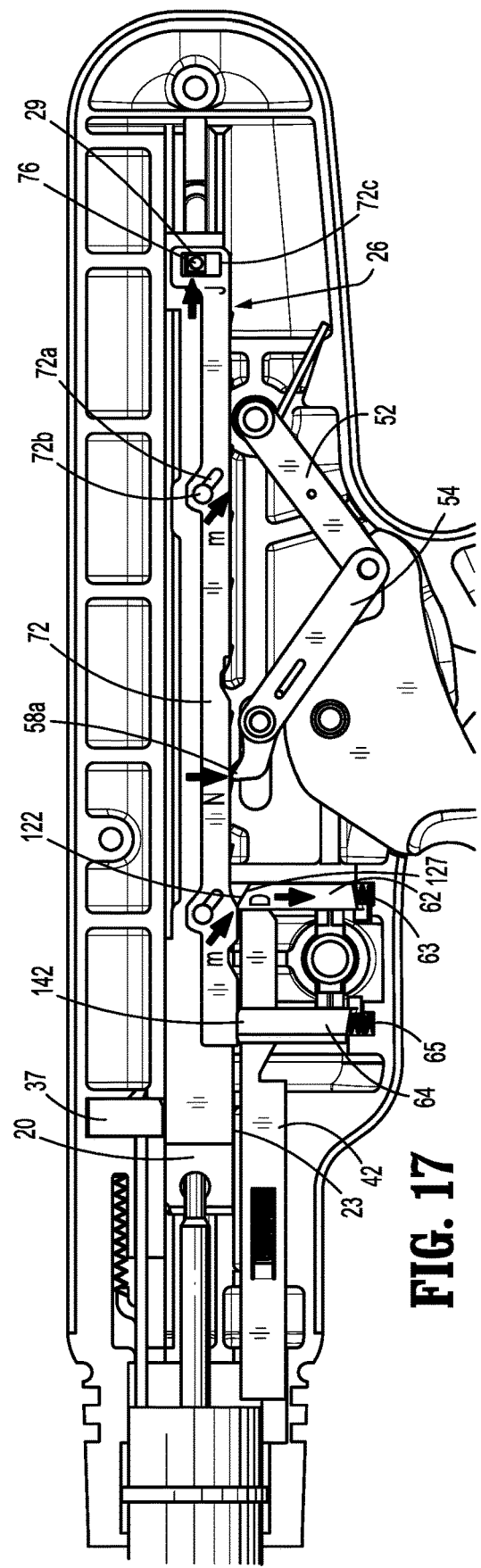

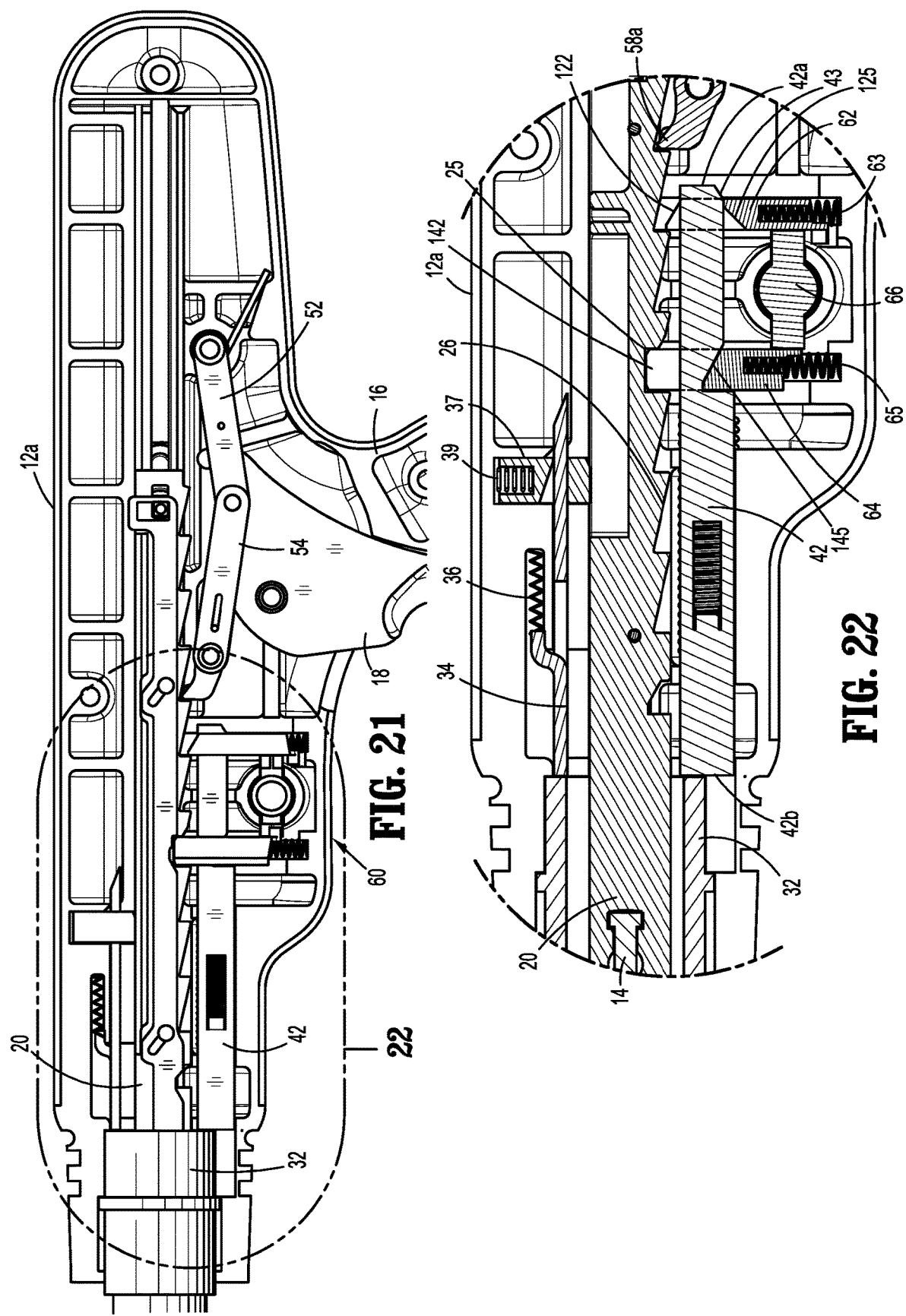

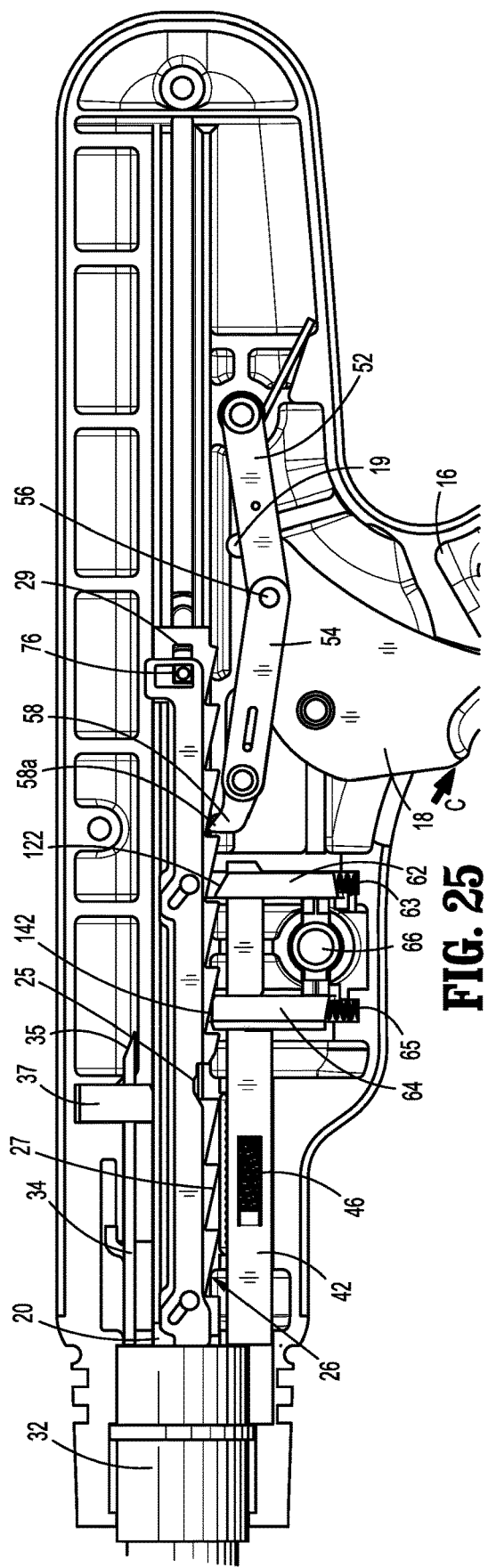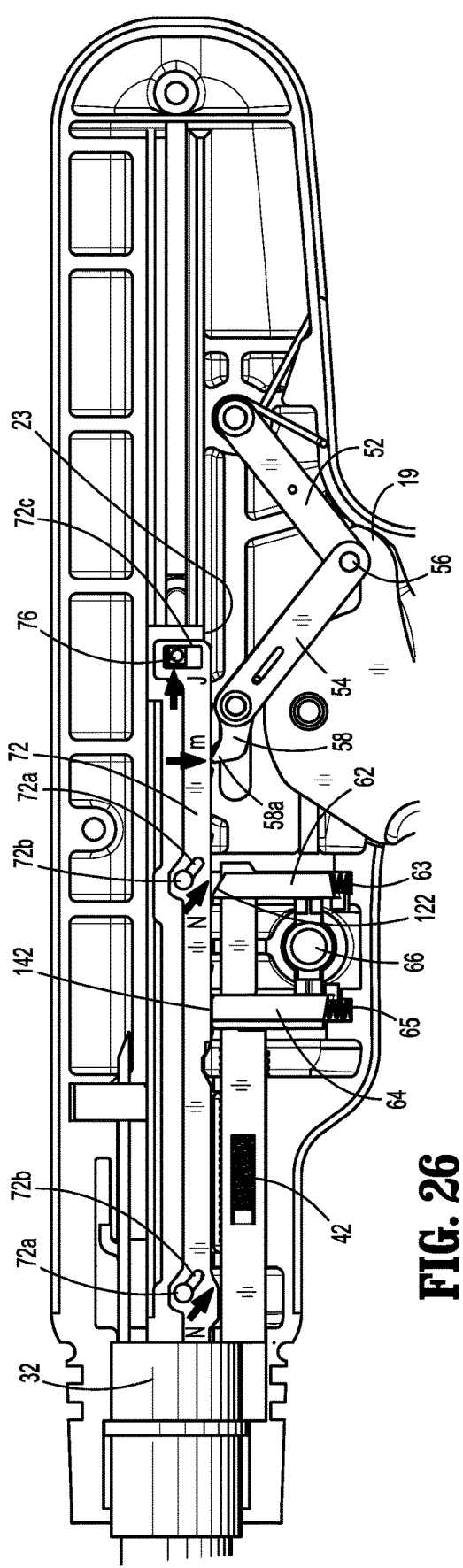

UNIVERSAL HANDLE FOR SURGICAL INSTRUMENTS

CROSS-REFERENCE TO RELATED APPLICATIONS

This application is a National Stage Application of PCT/CN2015/073116 under 35USC § 371 (a), the disclosure of the above-identified application is hereby incorporated by reference in its entirety.

BACKGROUND

1. Technical Field

The present disclosure relates to surgical instruments and, more specifically, to handles for manipulating end effectors of surgical instruments.

2. Discussion of Related Art

Surgical staplers have been developed for joining adjacent tissue, for providing hemostasis of adjacent tissue, and for providing hemostasis in conjunction with cutting of adjacent tissue. Such surgical staplers include, inter alia, linear and circular type configurations. Typically, linear staplers include parallel rows of staples with a slot for a cutting device to travel between the rows of staples. Examples of known linear staplers are disclosed in commonly assigned U.S. Pat. No. 6,045,560 to McKean et al., U.S. Pat. No. 6,032,849 to Mastri et al., and U.S. Pat. No. 5,964,394 to Robertson, the entire contents of each of which are incorporated herein by reference. Typically, circular staplers include a plurality of annular rows of staples (e.g., two annular rows of staples) and an annular blade disposed internally of the rows of staples. Examples of known circular staplers are disclosed in commonly assigned U.S. Pat. Nos. 5,799,857 and 5,915,616 to Robertson et al., the entire contents of each of which are incorporated herein by reference. These types of surgical staplers secure adjoining body tissue for improved cutting, join layers of tissue to one another and provide hemostasis by applying parallel or annular rows of staples to surrounding tissue as the cutting means cuts between the parallel or annular rows. Accordingly, by enabling a surgeon to perform all of these tasks simultaneously, surgical staplers have been effective in decreasing the amount of time it takes to fasten tissue together.

Linear and circular type staplers generally require different handles for firing each type of stapler. In a linear type stapler, a drive rod is generally advanced to clamp tissue between jaw members and then the drive rod is further advanced to sequentially fire the staples. The typical force required to fire a typical linear type stapler is about 150 pounds force ($lb_f$). In contrast, in a circular type stapler, a clamping shaft is generally retracted to retract an anvil that clamps tissue between the anvil and the staple cartridge and then a drive rod is advanced to fire all the staples simultaneously. The typical force required to fire a typical circular type stapler is about 600 $lb_f$. Accordingly, a hospital, medical facility, or surgical field kit is required to stock different handles for each type of stapler which increases the cost of surgical procedures and of inventory.

A handle may be used multiple times during a single surgical procedure by removing and replacing staple cartridges of an end effector (e.g., linear or circular staple cartridges) or by removing and replacing a loading unit from a handle (e.g., linear or circular single use loading units).

It would be beneficial to provide a single handle which is usable with different types of stapling devices.

SUMMARY

In an aspect of the present disclosure, a universal surgical handle includes a body having a moveable handle, an elongate member extending distally from the body to define a longitudinal axis, an actuation shaft, and a fire lock mechanism. The actuation shaft defines first and second lock slots spaced axially apart. The moveable handle is operatively associated with the actuation shaft to effect longitudinal movement of the actuation shaft. The fire lock mechanism has a lock pawl that is received within the first lock slot during a first mode of operation of the handle to lock the actuation shaft in a first longitudinal position and is received within the second lock slot during a second mode of operation of the handle to lock the actuation shaft in a second longitudinal position. The handle is adapted to transition from a home position to the first or second mode of operation in response to a loading unit being coupled to the elongate member.

In aspects, the handle is transitioned from the home position to the first mode of operation in response to a first loading unit type being coupled to the elongate member and is transitioned from the home position to the second mode of operation in response to a second loading unit type being coupled to the elongate member. The first loading unit type may be a linear type loading unit and the second loading unit type may be a circular loading unit.

In some aspects, the handle includes a drive rod extending through the elongate member. The elongate member has proximal and distal ends. The proximal end of the rod is coupled to the distal end of the actuation shaft such that longitudinal movement of the actuation shaft effects longitudinal movement of the drive rod.

In particular aspects, the handle includes a detection link that is translatable between a first position and a second position that is proximal to the first position in response to a loading unit being coupled to the elongate member. The detection link is configured to transition the handle between the first mode of operation when the detection link is in the first position and the second mode of operation when the detection link is in the second position. The fire lock mechanism may include a first lock pawl that is configured to lock the actuation shaft in the first longitudinal position during the first mode of operation and a second lock pawl that is configured to lock the actuation shaft in the second longitudinal position during the second mode operation. The first and second lock pawls may be biased towards the actuation shaft. The detection link may be configured to prevent the second lock pawl from being received in the second lock slot during the first mode of operation. The second lock pawl may define a detection link passage that slidably receives the detection link. The detection link may engage a lower surface of a portion of the second lock pawl that defines the detection link passage to prevent the second lock pawl from engaging the actuation shaft when the detection link is in the first position. The first lock pawl may be positioned proximal to the detection link when the detection link is in the first position such that the first lock pawl engages the actuation shaft.

In certain aspects, the first lock pawl is receivable in the first lock slot of the actuation shaft during the first mode of operation to lock the actuation shaft in the first longitudinal position. The detection link may be configured to prevent the first lock pawl from being received in the first lock slot during the second mode of operation. The first lock pawl may define a detection link channel that slidably receives the detection link. The detection link may engage a lower surface of a portion of the first lock pawl that defines the detection link channel engaging the detection link to prevent the first lock pawl from engaging the actuation shaft when the detection link is in the second position. The detection link may define a locking recess in a lower surface thereof. The second lock pawl may define a detection link passage that slidably receives the detection link. The locking recess of the detection link may be positioned within the detection link passage of the second lock pawl when the detection link is in the second position such that the second lock pawl engages the actuation shaft.

In aspects, the fire lock mechanism includes a fire button that is positioned between the first and second lock pawls. The fire button may be depressible to move the first lock pawl out of engagement with the actuation shaft when the actuation shaft is in the first longitudinal position during the first mode of operation and the fire button may be depressible to move the second lock pawl out of engagement with the actuation shaft when the actuation shaft is in the second longitudinal position during the second mode of operation. The fire button may define an axis that is traverse to the longitudinal axis and may be depressible along the transverse axis.

In some aspects, the first lock pawl includes camming protrusions protruding distally from a distal face thereof which define a cam slot therebetween. The fire button may include a first cam protruding proximally and positioned within the cam slot when the fire button is in a neutral position. The first cam may engage one of the camming protrusions of the first lock pawl when the fire button is move to a depressed position when the actuation shaft is in the first longitudinal position during the first mode of operation to remove the first lock pawl from the first lock slot of the actuation shaft.

In certain aspects, the second lock pawl includes camming protrusions that protrude proximally from a proximal face thereof which define a cam slot therebetween. The fire button may include a second cam that protrudes proximally and positioned within the cam slot when the fire button is in a neutral position. The second cam of the fire button may engage one of the camming protrusions of the second lock pawl when the fire button is moved to a depressed position when the actuation shaft is in the second longitudinal position during the second mode of operation to remove the second locking pawl from the second lock slot of the actuation shaft.

In particular aspects, handle includes a rack lock positioned distal to the actuation shaft when the handle is in the home position and the actuation shaft is in a fully retracted position that is proximal to the first and second longitudinal positions. The rack lock may be configured to engage the actuation shaft to prevent distal movement of the actuation shaft from the fully retracted position. The handle may include a rack release that is moveable in a direction parallel to the longitudinal axis of the elongate member to move the rack lock out of engagement with the actuation shaft.

In another aspect of the present disclosure, a surgical instrument includes a universal surgical handle and a loading unit. The universal surgical handle includes a body having a moveable handle, an elongate member extending distally from the body to define a longitudinal axis, an actuation shaft, and a fire lock mechanism. The actuation shaft defines first and second lock slots spaced axially apart. The moveable handle is operatively associated with the actuation shaft to effect longitudinal movement of the actuation shaft. The fire lock mechanism has a lock pawl that is received within the first lock slot during a first mode of operation of the handle to lock the actuation shaft in a first longitudinal position and is received within the second lock slot during a second mode of operation of the handle to lock the actuation shaft in a second longitudinal position. The loading unit is coupled to the elongate member and the universal surgical handle is in one of the first or second mode of operation in response to the loading unit being coupled to the elongate member.

In aspects, the universal surgical handle includes a plunger that is positioned about the longitudinal axis distal to the actuation shaft. The plunger may be translatable along the longitudinal axis of the elongate member. The loading unit may engage the plunger when the loading unit is coupled to the universal surgical handle to move the plunger towards the actuation shaft. The universal surgical handle may include a rack lock that is positioned distal to the actuation shaft when the actuation shaft is in a fully retracted position. The fully retracted position of the actuation shaft is proximal to the first and second longitudinal positions of the actuation shaft. The rack lock may be configured to lock the actuation shaft in the fully retracted position. The loading plunger may be configured to engage the rack release when the loading unit is coupled to the handle to move the rack lock to unlock the actuation shaft.

In some aspects, when the loading unit is a first loading unit type, the plunger is moved from a home plunger position to a first plunger position. In the first plunger position, the plunger engages the rack release to move the rack lock to unlock the actuation shaft and the handle is in the first mode of operation. When the loading unit is a second loading unit type, the plunger is moved from the home plunger position to a second plunger positioned that is proximal to the first plunger position. In the second plunger position, the plunger engages the rack release to move the rack lock to unlock the actuation shaft and engage the detection link to transition the universal surgical handle to the second mode of operation. The first loading unit type may be a linear loading unit and the second loading unit type may be a circular loading unit.

In another aspect of the present disclosure, a universal surgical handle includes a housing, an actuation shaft, a moveable handle, and an advancement mechanism. The actuation shaft is disposed within the housing and defines a longitudinal axis. The actuation shaft has a toothed rack. The moveable handle is supported on the housing and is moveable through an actuation stroke. The advancement mechanism includes first and second links. A first end of the first link is fixed relative to the housing and a second end of the first link is coupled to a first end of the second link by a drive pin. A second end of the second link is coupled to a drive pawl. The moveable handle is moveable into engagement with the advancement mechanism during the actuation stroke to move the first and second links from a misaligned position to an aligned position to advance the drive pawl from a proximal-most position to a distal-most position. The drive pawl is positioned to engage the toothed rack during movement from the proximal-most position to the distal most position to advance the actuation shaft within the housing. The drive pawl engaging a first tooth of the toothed rack during a first actuation stroke and the drive pawl engaging a second tooth of the toothed rack during a second actuation stroke of the moveable handle. The first tooth is sized to prevent the drive pawl from engaging the second tooth before the first actuation stroke is completed.

In aspects, the first and second links are biased towards the misaligned configuration. The advancement mechanism may include a link pin that is inserted through the first end of the first link to fix the first link relative to the housing. The advancement mechanism may also include a biasing member that is disposed about the link pin and engaged with the first link to bias the first and second links towards the misaligned configuration. The moveable handle may include a drive member that engages the drive pin. Each tooth of the toothed rack may have a length that is equal to the distance between the proximal-most and distal-most positions of the drive pawl along the longitudinal axis.

In some aspects the advancement mechanism includes a pawl pin that couples the second end of the second link to the drive pawl. The housing may device a slot parallel to the longitudinal axis. The pawl pin may be disposed within the slot to limit movement of the second end of the second link to movement in a direction parallel to the longitudinal axis.

In certain aspects, a geometry of the first and second links changes a handle force applied to the drive pin by the moveable handle to a drive force applied to the actuation shaft by the drive pawl. The handle force may be changed by a factor in a range of 1.0 to 6.0 to the drive force. Each tooth may have a length of 9 mm. Each actuation stroke of the moveable handle may advance the actuation shaft 9*mm*.

In another aspect of the present disclosure, the surgical instrument includes a universal handle having a housing, an actuation shaft, a moveable handle, and an advancement mechanism. The actuation shaft is disposed within the housing and defines a longitudinal axis. The actuation shaft has a toothed rack. The moveable handle is supported on the handle as is moveable through and actuation stroke. The advancement mechanism includes first and second links. The first link is fixed relative to the housing and the second end of the first link is coupled to a first end of the second link by a drive pin. A second end of the second link is coupled to a drive pawl. The moveable handle is moveable into engagement with the advancement mechanism during the actuation stroke to move the first and second links from a misaligned position to an aligned position. The drive pawl is positioned to engage the toothed rack during movement from the proximal-most position to the distal-most position to advance the actuation shaft when the drive pawl is advanced within the housing. The drive pawl engages a first tooth of the toothed rack during a first movement of the drive pawl from the proximal-most position to the distal-most position. During a second actuation stroke of the moveable handle, the drive pawl engages a second tooth of the toothed rack that is proximal to the first tooth during a second movement of the drive pawl from the proximal-most position to the distal-most position. The first tooth sized to prevent the drive pawl from engaging the second tooth before the drive pawl reaches the distal-most position and the first actuation stroke is completed. The loading unit is selectively coupled to the handle.

In aspects, the loading unit includes a circular stapling end effector. Alternatively, the loading unit may include a linear stapling end effector.

It may be advantageous to adapt a handle for use with both linear and circular type staplers. Such a handle may reduce the number of items in the inventory of a hospital, medical facility, or a surgical field kit and thus, reduce the cost of surgical procedures and the cost of inventory. In addition, such a handle may reduce the size of a surgical field kit.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 6 is a cross-sectional view taken along the section line 6-6 of FIG. 5;

FIG. 7 is an enlarged view of the indicated area of detail of FIG. 3;

FIG. 9 is a partial cross-sectional side view of the universal handle of FIG. 8 when a linear loading unit is attached;

FIG. 10 is a side view of the universal handle of FIG. 8 with a portion of the body removed and the moveable handle actuated and in a linear clamped position;

FIG. 11 is a side view of the universal handle of FIG. 8 in the linear clamped position with the moveable handle released;

FIG. 12 is a lower perspective view of the fire lock assembly of the universal handle of FIG. 11 with the circular fire lock pawl removed;

FIGS. 13 and 14 are a lower perspective view and a side view of the fire lock assembly of FIG. 12 with the fire button depressed;

FIGS. 15 and 16 are side views of the universal handle of FIG. 8 in a fired position;

FIG. 17 is a side view of the universal handle of FIG. 8 in a fired position with the retraction mechanism pulled proximally;

FIG. 21 is a side view of the universal handle of FIG. 18 with the moveable handle actuated and in a circular clamped position;

FIG. 22 is an enlarged cross-sectional side view of the indicated area of detail of FIG. 21;

FIG. 25 is a side view of the universal handle of FIG. 23 in a fired position;

and

Figure 1:
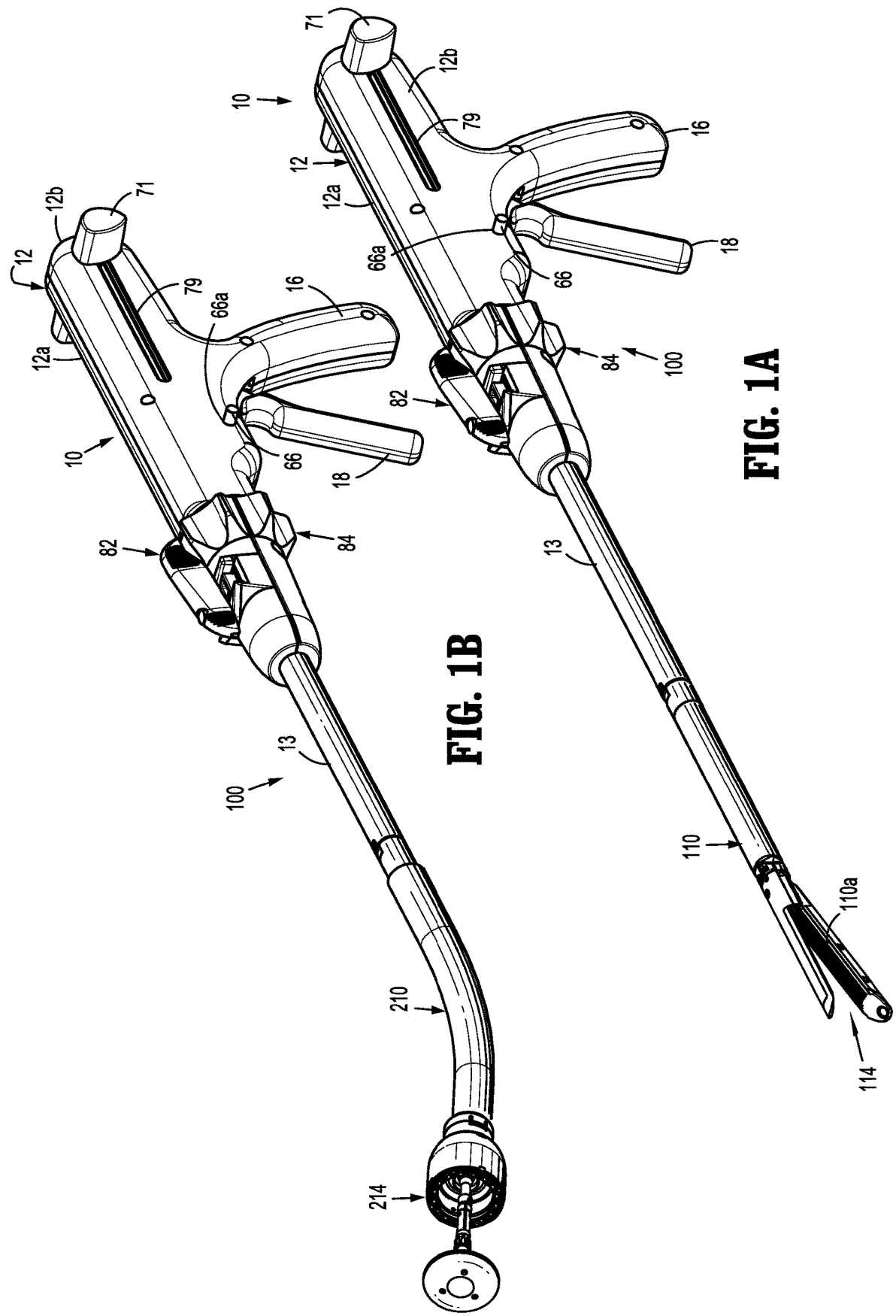
FIGS. 1A and 1B are perspective views of an embodiment of a manually actuated universal handle in accordance with the present disclosure coupled to a linear loading unit and a circular loading unit respectively.

FIG. 26 is a side view of the universal handle of FIG. 25 in a fired position with the retraction mechanism pulled proximally.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of a device or component of the device that is closest to the clinician and the term "distal" refers to the portion of a device or component of the device that is farthest from the clinician.

According to aspects of this disclosure, a manual universal handle (MUH) is configured to detect and fire both linear and circular type loading units releasably coupled the MUH. The loading units may be single or multiple use loading units and may include replaceable staple cartridges.

Referring to FIGS. 1A and 1B, a surgical instrument 100 includes a handle 10 and a linear loading unit 110 (FIG. 1A) or a circular loading unit 210 (FIG. 1B)). As described in detail below, the handle 10 is a MUH that is adapted to function in a first mode of operation when a linear loading unit 110 is coupled to the handle 10 and a second mode of operation when a circular loading unit 210 is coupled to the handle 10. The handle 10 includes a body 12 formed from two housing shells 12a, 12b that are coupled together. The housing shells 12a, 12b may be coupled together by any known means including, but not limited to, screwing, ultrasonic welding, or gluing. The handle 10 includes an elongate member 13 distally extending from the body 12. The elongate member 13 defines a longitudinal axis. The body 12 includes a fixed handle 16 and a moveable handle 18. Each loading unit 110, 210, is releasably coupled to and supported on the distal end of the elongate member 13. The linear loading unit 110 includes a linear stapling end effector 114 and the circular loading unit 120 includes a circular stapling end effector 214 which each are configured to clamp tissue and subsequently staple and/or cut tissue as detailed below.

The handle 10 may include an articulation control assembly 82 that articulates a distal end of a loading unit 110, 210 relative to the elongate member 13. In addition, the handle 10 may include a rotation control assembly 84 that rotates the elongate member 13 relative to the body 12. Such articulation control assemblies and rotation control assemblies are disclosed in commonly owned U.S. Pat. Nos. 5,865,361 and 7,967,178, the contents of each are hereby incorporated herein by reference in its entirety.

Figure 2:
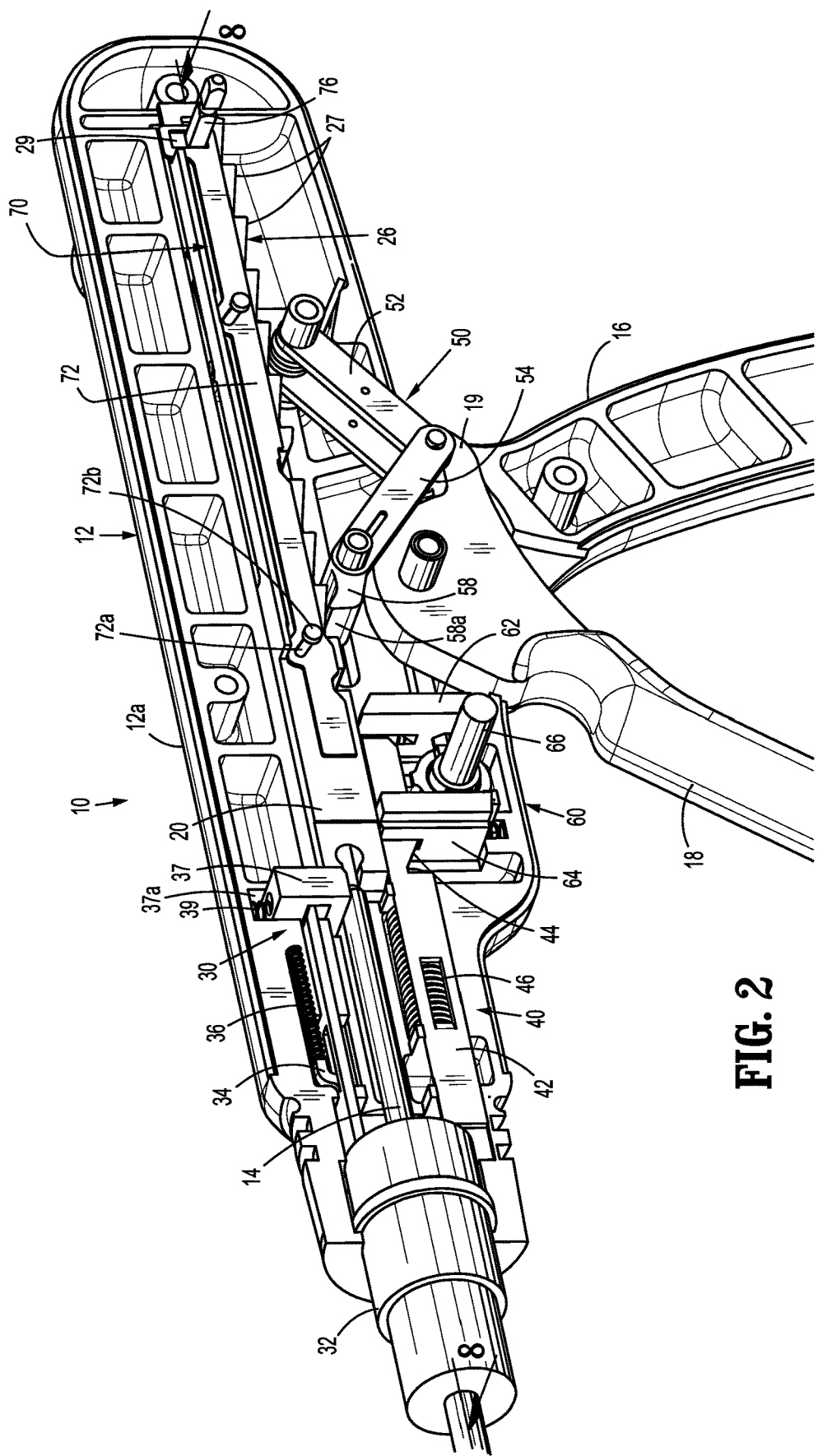
FIG. 2 is a perspective view of the universal handle of FIGS. 1A and 1B with a portion of the body removed.

With additional reference to FIGS. 2 and 3, the handle 10 includes a drive rod 14 that is longitudinally translated within the elongate member 13 to actuate the end effector 114, 214 of the loading unit 110, 210 to clamp and fire staples (not shown) through tissue as detailed below. The drive rod 14 is advanced from a fully retracted or home position, to a clamped position, and subsequently to a fired position as also detailed below. The drive rod 14 may also actuate the end effector to advance a knife (not shown) through the end effector which severs tissue clamped within the end effector during or after firing staples.

The handle 10 includes an actuation shaft 20, a rack locking mechanism 30, a loading unit detection mechanism 40, an advancement mechanism 50, a fire lock assembly or mechanism 60, and a retraction mechanism 70. The actuation shaft 20 is supported within the body 12 for linear translation and is coupled to the drive rod 14 such that longitudinal translation of the actuation shaft 20 effects longitudinal translation of the drive rod 14 along the longitudinal axis.

Figure 3:
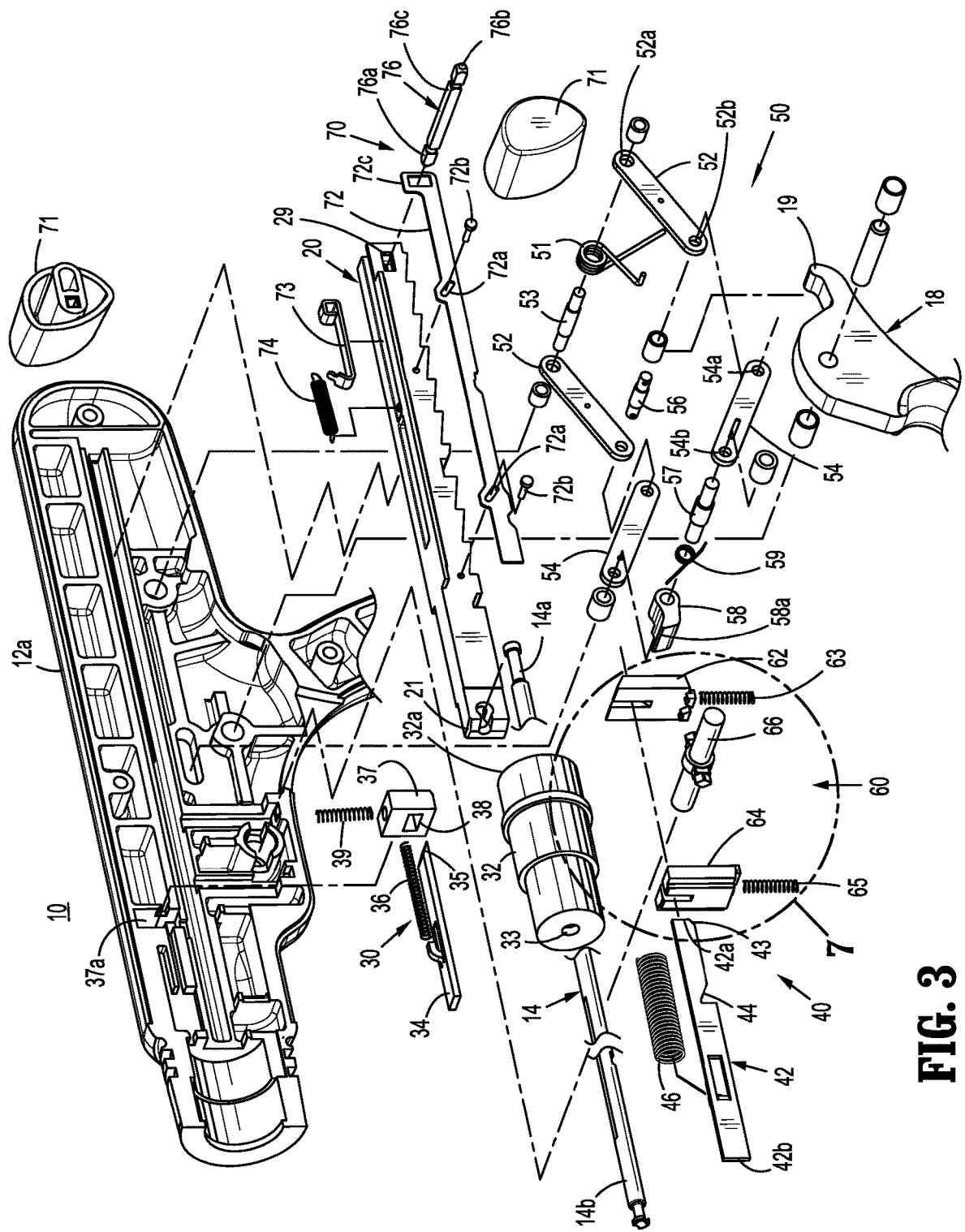
FIG. 3 is an exploded perspective view showing the components of the universal handle of FIG. 2.
Figure 4:
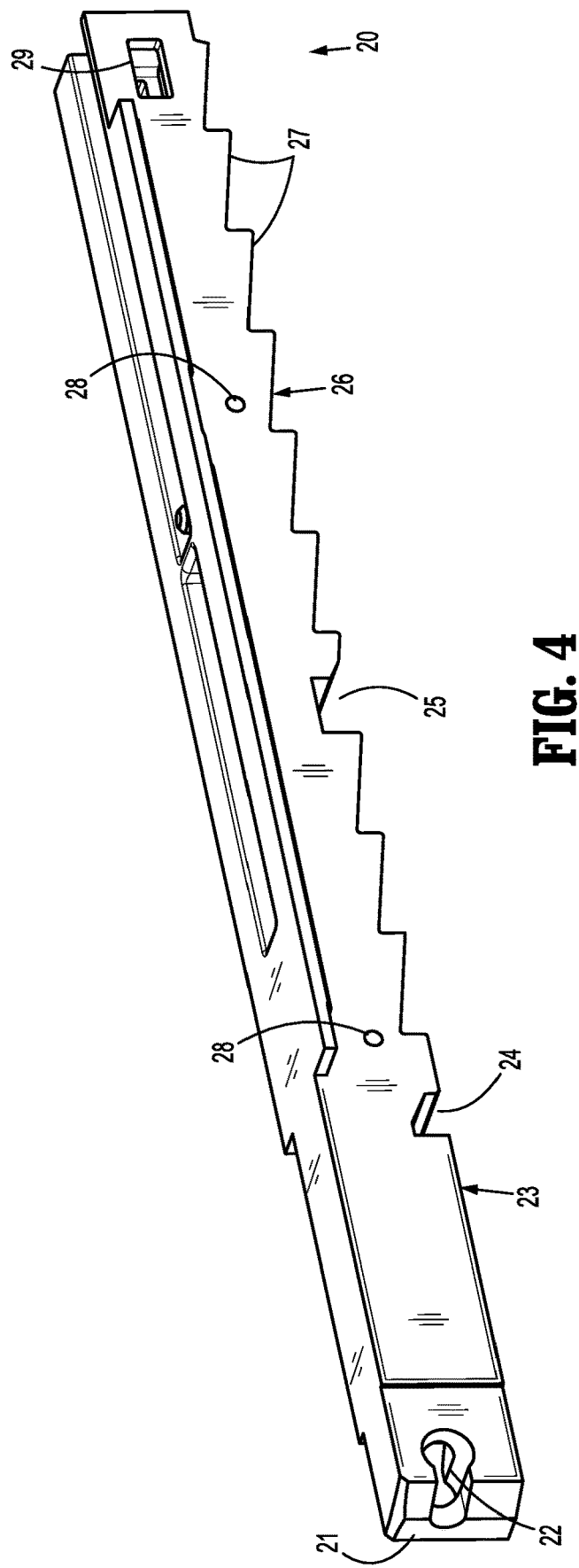
FIG. 4 is a view of the actuation shaft of FIG. 3.

Referring also to FIG. 4, the actuation shaft 20 includes a distal end 21 that defines a drive rod recess 22. The distal rod recess 22 receives a proximal end 14a (FIG. 3) of the drive rod 14 to couple the actuation shaft 20 to the drive rod 14. A lower surface 23 of the actuation shaft 20 defines a linear fire lock slot 24, a circular fire lock slot 25, and a toothed rack 26 having teeth 27. The linear fire lock slot 24 is positioned distal to the toothed rack 26 and the circular fire lock slot 25 is defined along the length of the toothed rack 26. The circular fire lock slot 25 is positioned proximal to the linear fire lock slot 24. It is contemplated that the circular fire lock slot 25 may be positioned distal to the toothed rack 26 as will be discussed in further detail below. The actuation shaft 20 defines pin holes 28 in a side surface thereof and a retraction slot 29 adjacent a proximal end thereof.

The rack locking mechanism 30 (FIG. 3) prevents longitudinal advancement of the actuation shaft 20 if a loading unit 110, 210 (FIGS. 1A and 1B) has not been coupled to the handle 10 via the elongate member 13. The rack locking mechanism 30 includes a loading plunger 32, a rack release member 34, and a rack lock 37. The loading plunger 32 defines a passage 33 which slidably receives the drive rod 14 such that the loading plunger 32 is disposed about drive rod 14 along the longitudinal axis of the elongate member 13. The rack release member 34 is biased proximally by a rack release biasing member 36 and engages a proximal surface 32a of the loading plunger 32 to urge the loading plunger 32 distally. The rack release member 34 includes a release finger 35 extending proximally towards the rack lock 37. The rack lock 37 is slidably disposed within a vertical slot 37a defined between housing shells 12a, 12b such that the rack lock 37 is longitudinally fixed in relation to the longitudinal axis but is movable along an axis transverse to the longitudinal axis.

Figure 8:
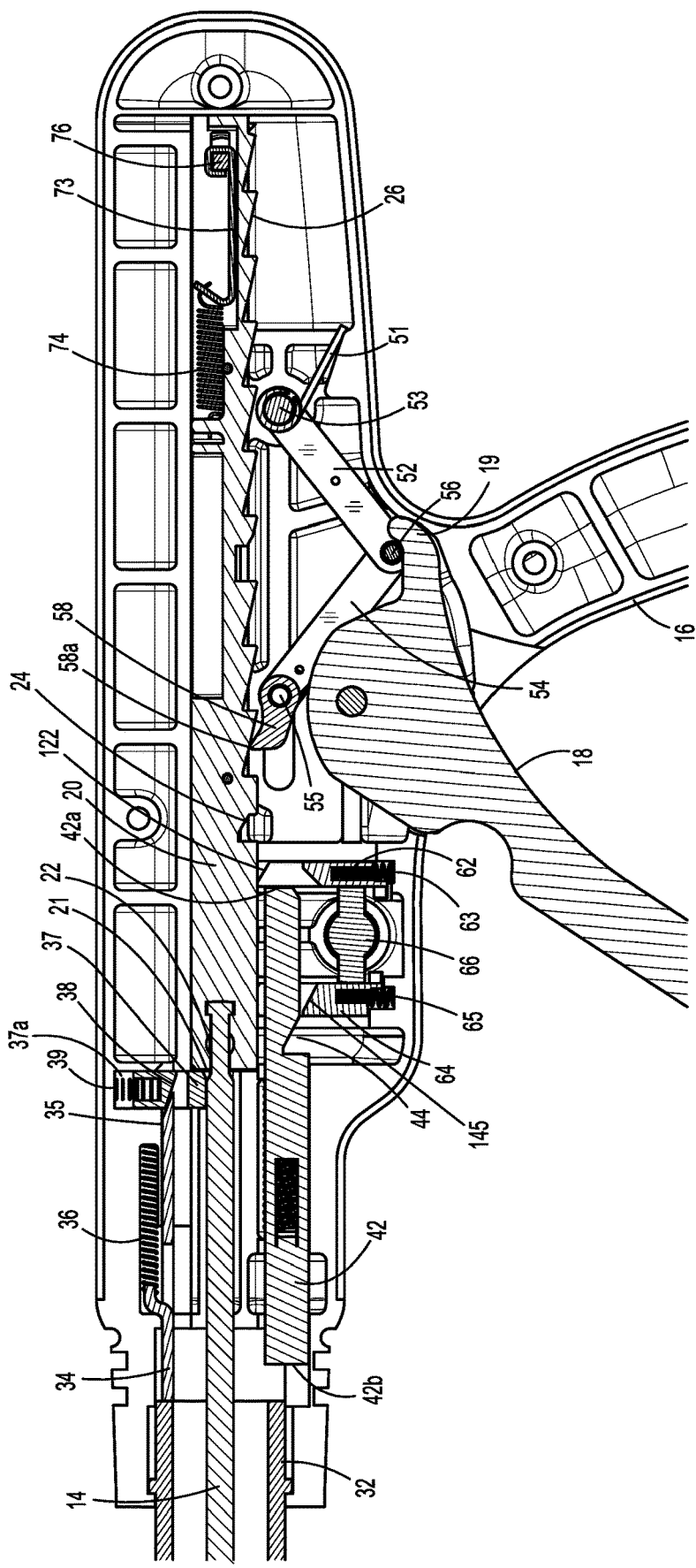
FIG. 8 is a side cross-sectional view taken along the section line 8-8 of FIG. 2.

The rack lock 37 defines a release slot 38 that is configured to slidably receive the release finger 35 of the rack release member 34. The rack lock 37 is urged downward by a rack lock biasing member 39 that is supported by the body 12 within vertical slot 37a. The upper surface of the release slot 38 may be angled and the release finger 35 may include an angled surface such that as the release finger 35 is proximally translated through the release slot 38, the angled surface of the release finger 35 engages the angled upper surface of the release slot 38 to move the rack lock 37 upward within the vertical slot 37a against the rack lock biasing member 39 (FIG. 8).

Figure 5:
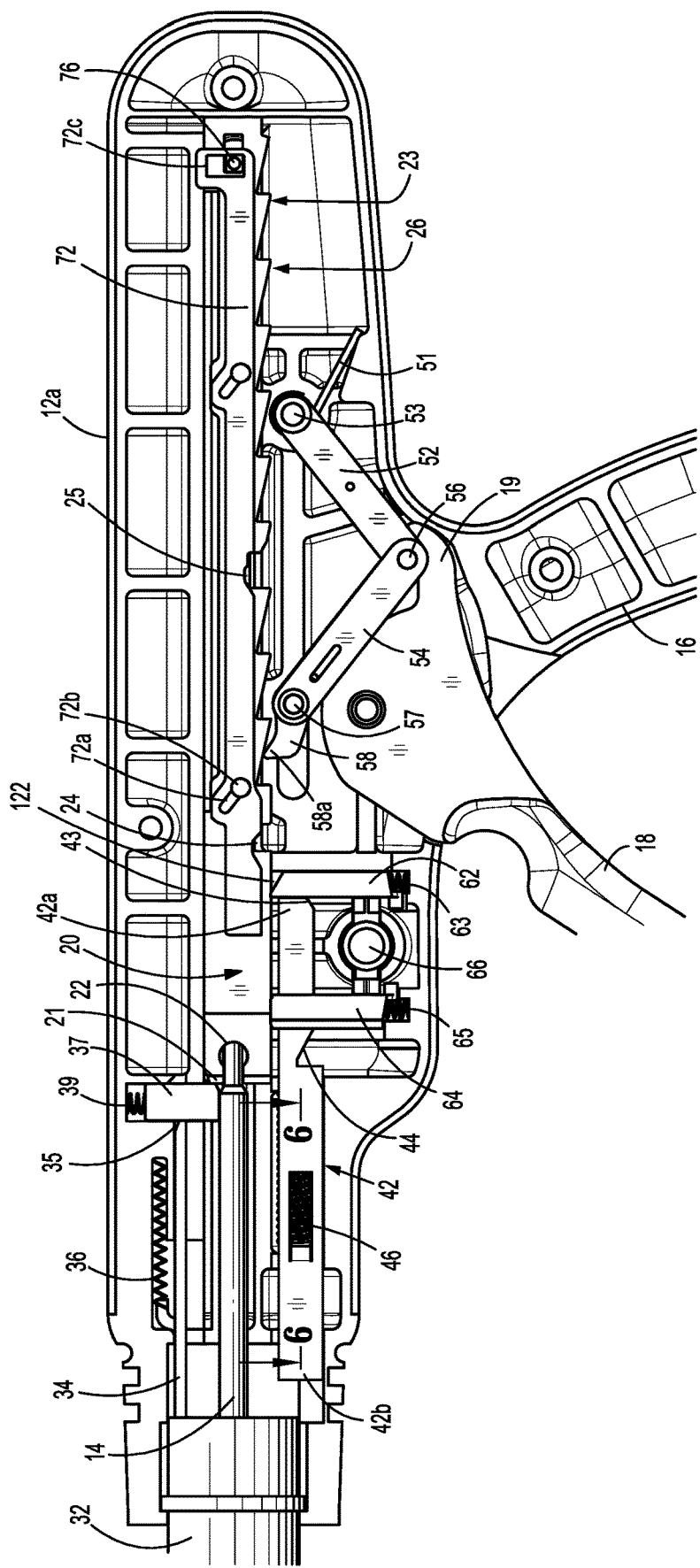
FIG. 5 is a side view of the universal handle of FIG. 2 with a portion of the body removed in a home position.
Figure 19:
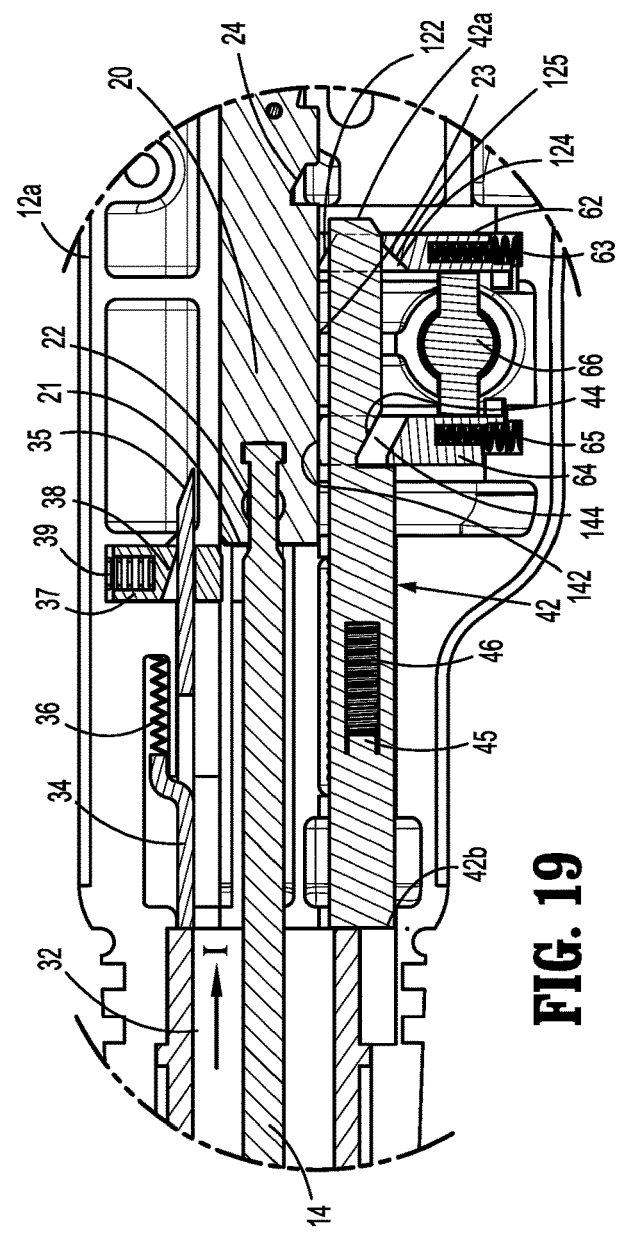
FIG. 19 is an enlarged cross-sectional side view of the indicated area of detail of FIG. 18.

Referring also to FIGS. 3, 5 and 6, the loading unit detection mechanism 40 detects when a circular loading unit 210 has been coupled to the handle 10 and then translates the advancement mechanism 50 to the second mode of operation. The loading unit detection mechanism 40 includes a detection link 42 that is slidably supported within the body 12 between a first position (FIG. 5) and a second position (FIG. 19). The detection link 42 is slidable along an axis parallel to the longitudinal axis and includes proximal and distal ends 42a, 42b. The proximal end 42a of the detection link 42 may include a chamfered surface 43. The detection link 42 defines a circular locking recess 44 in a lower surface thereof between the proximal and distal ends 42a, 42b. The detection link 42 further includes a retention tab 45 (FIG. 6) that engages the housing portion 12a to limit distal translation of the detection link 42. The loading unit detection mechanism 40 includes a detection link biasing member 46 that engages the retention tab 45 to urge the detection link 42 distally towards the first position.

The distal end 42b of the detection link 42 is engaged by the loading plunger 32 when a circular loading unit 210 is coupled to the handle 10 to proximally translate the detection link 42 towards the second position (FIG. 19). When the detection link 42 is translated proximally within the handle 10, the proximal end 42a of the detection link 42 engages the fire lock mechanism 60 to translate the advancement mechanism 50 to the second mode of operation as detailed below.

Referring again to FIGS. 2 and 3, the advancement mechanism 50 effects advancement of the actuation shaft 20 in response to actuation of the moveable handle 18, i.e., movement of the movable handle 18 from an initial or uncompressed position spaced apart from the fixed handle 16 towards the fixed handle 16, to clamp and fire staples through tissue as detailed below. The advancement mechanism 50 includes a pair of first links 52, a pair of second links 54, a drive pin 56, and a drive pawl 58. The first links 52 include a first end 52a rotatably supported about a first link pin 53. The first link pin 53 is fixed relative to and supported by the body 12. The advancement mechanism 50 may include a first link biasing member 51 disposed over the first link pin 53. The first link biasing member 51 may be in the form of a torsion spring having a first end that engages the first links 52 and a second end that engages the body 12 (FIG. 16) to urge the moveable handle 18 towards the uncompressed position (i.e., a position spaced from the fixed handle 16). The first links 52 include a second end 52b and the second links 54 include a first end 54a which are rotatably coupled together about the drive pin 56. The second links 54 include a second end 54b having a pawl pin 57 rotatably supported therethrough. The pawl pin 57 rotatably supports the drive pawl 58. The advancement mechanism 50 may include a drive pawl biasing member 59 disposed about the pawl pin 57 to urge a drive finger 58a of the drive pawl 58 into engagement within the toothed rack 26 of the actuation shaft 20. The pawl pin 57 may be supported within a slot defined by the body 12 to slide parallel to the longitudinal axis of the drive rod 14 between a proximal-most position and a distal-most position. The moveable handle 18 includes a proximally extending hooked drive member 19 that is supported beneath and engages the drive pin 56 to advance the drive finger 58a of the drive pawl 58 into the toothed rack 26 of the actuation shaft 20 to advance the actuation shaft 20 as detailed below.

Referring also to FIG. 7, the fire lock mechanism 60 prevents the advancement mechanism 50 from advancing the actuation shaft 20 from a clamped position to a fired position without user intervention. The fire lock mechanism 60 includes a linear fire lock pawl 62, a circular fire lock pawl 64, and a fire button 66. A respective one of the linear fire lock pawl 62 or the circular fire lock pawl 64 engages the actuation shaft 20 when an end effector (e.g., end effector 114, 214 (FIGS. 1A and 1B)) is attached to a loading unit and moved to a clamped position. This prevents the inadvertent firing of staples and/or cutting of tissue as will be discussed in detail below. The linear fire lock pawl 62 engages the actuation shaft 20 during the first mode of operation (e.g., when the linear loading unit 110 is coupled to the handle 10) and the circular fire lock pawl 64 engages the actuation shaft 20 during the second mode of operation (e.g., when the circular loading unit 210 is coupled to the handle 10) to prevent advancement of the actuation shaft beyond a clamped position until the lock pawl 62, 64 is manually released.

The linear fire lock pawl 62 is supported within the body 12 and includes an upper surface 122 that engages the actuation shaft 20. The upper surface 122 of the linear fire lock pawl 62 may be urged into engagement with the actuation shaft 20 by a pawl biasing member 63 supported within the body 12. The upper surface 122 of the linear fire lock pawl 62 may be angled such that when the upper surface 122 is engaged with the toothed rack 26 of the actuation shaft 20 and the actuation shaft 20 is advanced, a tapered surface of the teeth 27 engage the angle of the upper surface 122 to slide along the upper surface 122 and urge the linear fire lock pawl 62 away from the actuation shaft 20, i.e., against the pawl biasing member 63. As the actuation shaft 20 is advanced the upper surface 122 can engage a vertical surface of each tooth 27 to prevent the actuation shaft 20 from retracting a distance greater than one tooth 27 as detailed below.

The linear fire lock pawl 62 includes camming protrusions 127 extending from a distal surface 126 thereof. The camming protrusions 127 define a cam slot 129 therebetween. Each of the camming protrusions 127 defines a notch 128 in an upper surface thereof. The fire button 66 is slidably disposed through openings 66a (FIG. 1) defined in the body 12 and includes a cam 164 protruding proximally from a midpoint of the fire button 66. The cam 164 positioned within the cam slot 129 when the fire button 66 is in a neutral or non-depressed position. When the fire button 66 is depressed during the first mode of operation (e.g., when a linear loading unit 110 is coupled to the handle 10), the cam 164 engages one of the camming protrusions 127 to move the linear fire lock pawl 62 downwardly against the pawl biasing member 63 and away from the actuation shaft 20. When this occurs, the upper surface 122 of the linear fire lock pawl 62 is positioned below and out of engagement with the linear fire lock slot 24 of the actuation shaft 20 to facilitate distal advancement of the actuation shaft 20. It is contemplated that when the firing button 66 is depressed during the first mode of operation of the handle 10, the upper surface 122 of the linear fire lock pawl 62 may engage portions of the actuation shaft 20 as the actuation shaft 20 is advanced over the linear fire lock pawl 62.

The linear fire lock pawl 62 defines a detection link channel 124 that is sized to slidably receive the detection link 42. As discussed above and described below in further detail, movement of the detection link 42 transitions the handle 10 between the first and second modes of operation. As the detection link 42 is slid through the detection link channel 124 in response to the coupling of a circular loading unit 210 to elongate member 13, the proximal end 42a of the detection link 42 engages a lower surface 125 of the detection link channel 124 to move the linear fire lock pawl 62 downwardly against the pawl biasing member 63 and out of engagement with the actuation shaft 20 as shown in FIG. 25. The lower surface 125 of the detection link channel 124 may be angled to be engaged by the chamfered surface 43 (FIG. 3) of the detection link 42. It will be appreciated that during the second mode of operation, the upper surface 122 of the linear fire lock pawl 62 may remain below and out of engagement with the actuation shaft 20.

The circular fire lock pawl 64 includes an upper surface 142 and defines a detection link passage 144. The upper surface 142 is urged upwardly towards the actuation shaft 20 by a pawl biasing member 65. The detection link passage 144 slidably receives the detection link 42 therethrough. As shown in FIG. 8, during the first mode of operation (e.g., when a linear loading unit 110 is coupled to the handle 10), the detection link 42 engages a lower surface 145 of the detection link passage 144 to prevent the upper surface 142 of the locking pawl 64 from engaging and locking the actuation shaft 20. It is contemplated that during the first mode of operation, the upper surface 142 may engage portions of the actuation shaft 20 as the actuation shaft 20 is advanced over the circular lock pawl 64.

During the second mode of operation (e.g., when a circular loading unit 210 is coupled to the handle 10), the portion of the detection link 42 defining the circular locking recess 44 of the detection link 42 is positioned within the detection link passage 144 of the circular fire lock pawl 64 such that the pawl biasing member 65 urges the upper surface 142 of the circular fire lock pawl 64 into engagement with the actuation shaft 20. As the actuation shaft 20 is advanced from the home position towards the fired position, the tapered surface of the teeth 27 slide along the upper surface 142 and urge the circular fire lock pawl 64 away from the actuation shaft 20, i.e., against the pawl biasing member 65. As the actuation shaft 20 is advanced the upper surface 142 can engage the vertical surface of each tooth 27 to prevent the actuation shaft 20 from retracting a distance greater than a length of a tooth 27 until the circular fire lock pawl 64 engages the circular fire lock slot 25.

The circular fire lock pawl 64 includes camming protrusions 147 extending from a proximal surface 146 thereof. The camming protrusions 147 define a cam slot 149 (FIG. 29) therebetween. Each of the camming protrusions 147 defines a notch 148 (FIG. 29) in an upper surface thereof. The fire button 66 includes a cam 166 protruding distally from a midpoint of the fire button 66. The cam 166 is positioned within the cam slot 149 when the fire button 66 is in a neutral or non-depressed position. When the fire button 66 is depressed during the second mode of operation of the handle 10 (e.g., when a circular loading unit 210 is coupled to the handle 10), the cam 166 engages one of the camming protrusions 147 to move the circular fire lock pawl 64 downwardly against the pawl biasing member 65 and away from the actuation shaft 20 such that the upper surface 142 of the circular lock pawl 64 is positioned below and out of engagement with the circular fire lock slot 25 of the actuation shaft 20 to permit the actuation shaft 20 to advance towards the fired position. As the actuation shaft 20 is advanced from the circular clamped position towards the fired position, the tapered surface of the teeth 27 may slide along the upper surface 142 of the circular lock pawl 64 and urge the circular fire lock pawl 64 away from the actuation shaft 20, i.e., against the pawl biasing member 65. As the actuation shaft 20 is advanced the upper surface 142 can engage the vertical surface of each tooth 27 to prevent the actuation shaft 20 from retracting a distance greater than a length of a tooth 27.

Referring again to FIGS. 1-3, the retraction mechanism 70 includes a retraction knobs 71 connected to the proximal end of actuation shaft 20 by a coupling rod 76. The coupling rod 76 includes right and left engagement portions (76a, 76b) for receiving retraction knobs 71 and a central portion 76c which is dimensioned and configured to translate within the retraction slot 29 formed adjacent the proximal end of the actuation shaft 20. The retraction mechanism 70 includes a release plate 72 mounted to the actuation shaft 20 by slide pins 72b inserted in the slide pin holes 28 defined in the side surface of the actuation shaft 20. The proximal end of the release plate 72 defines a transverse slot 72c to accommodate a central portion 76c of the coupling rod 76. The release plate 72 is mounted for movement with respect to the actuation shaft 20 in response to manipulation of the retraction knobs 71. More specifically, the slide pins 72b are received by an angled cam slots 72a formed in release plate 72. Proximal movement of the retraction knobs 71 effects proximal movement of the coupling rod 76 and thus, proximal movement of the release plate 72. As the release plate 72 moves proximally, the slide pins 72b cam release plate 72 downwardly with respect to actuation shaft 20 and with respect to toothed rack 26 such that the bottom portion of the release plate 72 extends below the toothed rack 26 to disengage the finger 58a of the drive pawl 58, the linear fire lock pawl 61, and the circular fire lock pawl 65 from engagement with the toothed rack 26 as shown in FIG. 17. The body 12 defines elongated slots 79 (FIGS. 1A and 1B) to accommodate the longitudinal translation of the coupling rod 76 as the retraction knobs 71 is pulled proximally to retract actuation shaft 20 and thus retract the control rod 14.

The coupling rod 76 is biased distally in relation to the actuation shaft 20 by a retraction biasing member 74 which is secured at one end to the coupling rod 76 via a connector 73 and at the other end to a portion of the actuation shaft 20. A similar retraction device is disclosed in commonly owned U.S. Pat. Nos. 6,330,965 and 7,967,178, each of which is incorporated herein by reference in their entirety.

FIGS. 5-17 illustrate operation of the handle 10 in the first mode of operation. FIGS. 5-8 illustrate, the actuation shaft 20 in a fully retracted position. The rack release member 34 is urged distally by the rack release biasing member 36 to engage the loading plunger 32 and move the loading plunger 32 distally. The rack lock 37 is urged downward by rack lock biasing member 39 within slot 37a to a locked position such that the rack lock 37 is engaged with the distal end surface 21 of the actuation shaft 20 to prevent longitudinal advancement of the actuation shaft 20 from the home position. In addition, the detection link biasing member 46 is engaged with the retention arm 45 (FIG. 6) of the detection link 42 to urge the detection link 42 distally. The retention arm 45 abuts a portion of the housing portion 12a to limit distal movement of the detection link 42 such that the distal end 42b of the detection link 42 is positioned proximal to the loading plunger 32 and the proximal end 42a of the detection link 42 is positioned distal to and outside of the detection link channel 124 (FIG. 7) of the linear fire lock pawl 62. The upper surface 122 of the linear fire lock pawl 62 is urged upward and into engagement with the actuation shaft 20 by the pawl biasing member 63 at a position distal to the linear clamping lock slot 24 of the actuation shaft 20.

With reference to FIG. 9, when a linear loading unit 110 is coupled to the handle 10, the linear loading unit 110 moves the rack release member 34 proximally against the rack release biasing member 36. As the rack release member 34 moves proximally, the release finger 35 of the rack release member 34 is slid through the release slot 38 formed through the rack lock 37 to move the rack lock 37 upward, as shown by Arrow R, against the rack lock biasing member 39. When the rack lock 37 is moved upward, the rack lock 37 moves out of engagement with the distal end surface 21 of the actuation shaft 20 to facilitate advancement of the actuation shaft 20 from the home position. It will be appreciated that when a linear loading unit 110 is coupled to the handle 10, the loading plunger 32 is not moved to a position to engage the distal end 42b of the detection link 42.

Referring now to FIG. 10, with the linear loading unit 110 is coupled to the handle 10, the moveable handle 18 is actuated, i.e., compressed, from an uncompressed or initial position towards the fixed handle 16 as shown by Arrow C. As the moveable handle 18 is actuated, the drive finger 19 of the moveable handle 18 engages the drive pin 56 to straighten the pairs of links 52, 54 and advance the drive pawl 58 into the teeth 27 of the actuation shaft 20 to advance the actuation shaft 20 as shown by the Arrow A (FIG. 10). The actuation shaft 20 is initially advanced to move the end effector 114 to the clamped position such that the linear fire lock pawl 62 is received in the linear fire lock slot 24. As shown, as the moveable handle 18 is actuated, the drive finger 19 engages the drive pin 56 to move the drive pin 56 upward such that the drive pawl 58 is moved distally by the second link 54.

The actuation shaft 20 is advanced until the upper surface 122 of the linear fire lock pawl 62 is received in the linear fire lock slot 24 formed in the lower surface 23 of the actuation shaft 20. When the upper surface 122 is received in with the linear fire lock slot 24, the end effector 114 of the loading unit 110 is in a clamped configuration (not shown) with tissue clamped therein. The linear fire lock pawl 62 prevents longitudinal translation (e.g., advancement or retraction) of the actuation shaft 20 beyond the clamped position when the upper surface 122 of the linear fire lock pawl 62 is received in the linear fire lock slot 24 to prevent inadvertent firing of the surgical instrument 100.

With reference to FIG. 11, with the upper surface 122 received in the linear fire lock slot 24, the moveable handle 18 is retracted away from the fixed handle 16 towards the initial or fully uncompressed position as shown by the Arrow U. It will be appreciated that the moveable handle 18 may be moved away from the fixed handle 16 by the first link biasing member 51 engaging the first link 52 to move the drive pin 56 against the drive finger 19 of the moveable arm 18. When the moveable handle 18 reaches the fully uncompressed position, the drive finger 58a of the drive pawl 58 engages a proximal surface of a first tooth 27a. Although the presently disclosed handle is configured to provide multiple actuations of the moveable handle 18 to effect clamping and firing of the end effector, it is envisioned that the handle 10 may be configured to effect clamping and firing with a single actuation of the movable handle 18.

Referring also to FIGS. 12-14, with the drive finger 58a of the drive pawl 58 engaged with the proximal surface of the first tooth 27a of the toothed rack 26 of the actuation shaft 20, the fire button 66 is depressed to move the fire button 66 from a rest or neutral position (FIG. 12) to a depressed position as shown by Arrow P (FIG. 13). As the fire button 66 is depressed, the cam 164 of the fire button 66 engages one of the camming protrusions 127 of the linear fire lock pawl 62 to move the linear fire lock pawl 62 downwardly away from the actuation shaft 20 as shown by Arrow D (FIGS. 13 and 14) such that the upper surface 122 of the linear fire lock pawl 62 is removed from the linear fire lock slot 24. When the fire button 66 is depressed, the cam 164 may be received within the notch 128 of the camming protrusion 127 to retain fire lock pawl 62 in a downward position against the pawl biasing member 63 such that the upper surface 122 of the linear fire lock pawl 62 is out of engagement with the lower surface 23 of the actuation shaft 20. It will be appreciated that the fire button 66 may be pressed in the direction represented by Arrow P or in a direction opposite the direction represented by Arrow P to allow for right or left handed operation of handle 10.

Referring to FIG. 15, with the upper surface 122 of the linear fire lock pawl 62 removed from the linear fire lock slot 24, the moveable handle 18 is moved towards the fixed handle 16 to advance the actuation shaft 20 with the drive pawl 58 a length L. The teeth 27 of the toothed rack 26 are sized such that each actuation of the moveable handle 18 from the fully uncompressed position (FIG. 11) to the fully compressed position (FIG. 13) advances the actuation shaft 20 a longitudinal distance equal to the length L, which is equal to the longitudinal length of each tooth 27.

It will be appreciated that the longitudinal length L of each tooth 27 is equal to the longitudinal distance that the actuation shaft 20 is advanced with each cycle or actuation of the moveable handle 18. Such an arrangement configures the handle 10 to prevent half-firing of the handle 10. Specifically, if the moveable handle 18 is released before reaching the fully compressed position, subsequent actuation of the moveable handle 18 from an uncompressed position towards the fixed handle completes the previous cycle of the moveable handle 18 (i.e., the moveable handle 18 must reach the fully compressed position before the drive finger 58a engages the next tooth 27 of the toothed rack 26). This prevents the handle 10 from half-firing a fastener or cartridge (not shown) before advancing to the next fastener or cartridge. For example, as shown in FIG. 15, the drive finger 58a is engaged with a proximal vertical surface of tooth 27a to advance the actuation shaft 27 such that if during an actuation of the moveable handle 18 the moveable handle 18 is released before reaching the fully compressed position during the next actuation of the moveable handle 18 the drive finger 58a reengages the proximal vertical surface of the tooth 27a until the moveable handle 18 reaches the fully compressed position. After the moveable handle 18 reaches the fully compressed position during the next actuation of the moveable handle 18, the drive finger 58a engages a proximal vertical surface of tooth 27b (FIG. 16).

The moveable handle 18 is actuated until all the staples or fasteners (not shown) of the cartridge 110 of the linear loading unit 110 are fired or a desired amount of tissue is stapled.

With reference to FIG. 17, when the all the staples are fired or a desired amount of tissue is stapled, the retraction knobs 71 (FIG. 1) are pulled to retract the actuation shaft 20 to the fully retracted position. As the retraction knobs 71 are pulled proximally (as shown by Arrow J), the coupling shaft 76 is moved proximally within the retraction slot 29 (FIG. 1) formed in the proximal end of the actuation shaft 20. As the coupling shaft 76 is moved proximally, the coupling shaft 76 engages the release plate 72 to move the release plate 72 proximally in relation to the slide pins 72b and actuation shaft 20 such that pins 72b move within the release slots 72a of the release plate 72 (as shown by Arrows M) to urge the release plate 72 downward (as shown by Arrow N). When the release plate 72 is moved downward, the release plate 72 moves below teeth 27 of the actuation shaft 20 and engages the drive finger 58a of the drive pawl 58 and the upper surface 122 of the linear fire lock pawl 62 to urge the drive pawl 58 and the linear fire lock pawl 62 out of engagement with the lower surface 23 of the actuation shaft 20 to facilitate retraction of the actuation shaft 20. The release plate 72 may also engage the upper surface 142 of the circular lock pawl 64 when the release plate 72 is moved below the lower surface 23 of the actuation shaft 20.

When the actuation shaft 20 is fully retracted and the loading unit 110, 210 is detached, the rack lock 37 is urged downwardly by the rack lock biasing member 39 into engagement with the distal end surface 21 of the actuation shaft 20 to lock the actuation shaft 20 in the fully retracted position. More specifically, when the loading unit 110, 210 is detached from the elongate member 13 of the handle 10, the biasing member 36 urges the rack release member 34 distally to move the release finger 35 from the release slot 38 of the rack lock 37. When the release finger 35 is withdrawn from the release slot 38, the biasing member 39 urges the rack lock 37 downwardly to a position distal of the actuation shaft 20. When the actuation shaft 20 is in the fully retracted position, the fired staple cartridge 110a (FIG. 1) may be replaced with a new, fresh, unfired staple cartridge in the loading unit 110, 210, the entire loading unit 110, 210 may be replaced with a new, fresh, unfired loading unit 110, 210, or the handle 10 may be sterilized for reuse with another patient. Alternatively, the handle 10 may be disposable.

FIGS. 18-26 illustrate the second mode of operation of the handle 10. As detailed above with respect to the first mode of operation, initially the handle 10 is in the home position with the actuation shaft 20 in a fully retracted position (FIG. 8).

Figure 18:
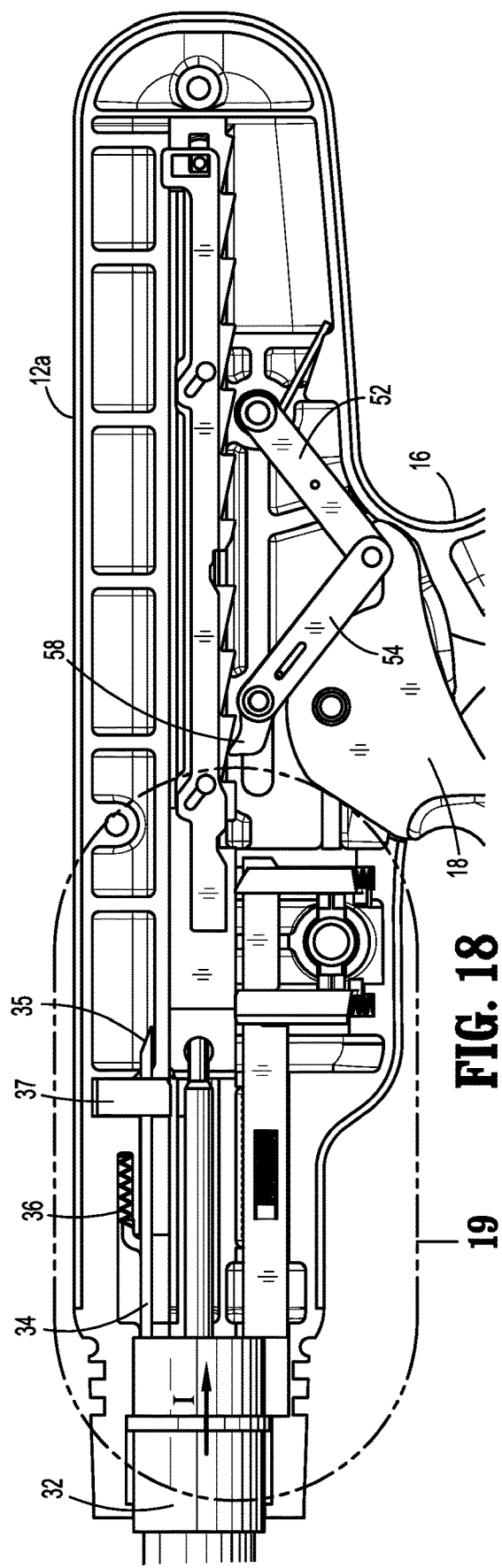
FIG. 18 is a side view of the universal handle of FIG. 8 when a circular loading unit is attached.

With reference to FIGS. 18 and 19, when a circular loading unit 210 configured to move the loading plunger 32 proximally (as shown by Arrow I) a second distance different from the first distance is coupled to handle 10, the loading plunger 32 is moved proximally to move the rack release member 34 proximally against the rack release biasing member 36. As the rack release member 34 moves proximally, the release finger 35 of the rack release member 34 slides through the release slot 38 formed through the rack lock 37 to move the rack lock 37 upward against the urging of the rack lock biasing member 39. When the rack lock 37 moves upward, the rack lock 37 moves out of engagement with the distal end surface 21 of the actuation shaft 20.

As the loading plunger 32 is moved proximally during the second mode of operation in response to coupling of the circular loading unit 210 to the handle 10, the loading plunger 32 engages the distal end 42b of the detection link 42 to move the detection link 42 proximally from a first position to a second position. In the second position of the detection link 42, the circular locking recess 44 formed in the detection link 42 is positioned within the detection link passage 144 defined in the circular fire lock pawl 64 (FIG. 19).

In addition, the proximal end 42a of the detection link 42 passes through the detection link channel 124 defined in the linear fire lock pawl 62 to move the linear fire lock pawl 62 downward against the urging of the pawl biasing member 63. It is contemplated that the proximal end 42a of the detection link 42 may engage the lower surface 125 of the detection link channel 124 to move the linear fire lock pawl 62 downward, against the urging of the pawl biasing member 63 as the detection link 42 passes through the detection link channel 124 such that the upper surface 122 of the linear fire lock pawl 62 is out of engagement with the lower surface 23 of the actuation shaft 20. When the detection link 42 is moved distally such that the locking recess 44 is positioned within the detection link passage 124 of the linear fire lock pawl 62, the upper surface 122 of the linear fire lock pawl 62 is prevented from engaging the linear fire lock slot 24 (FIG. 20) of the actuation shaft 20 to lock the actuation shaft 20 in the linear clamped position. It will be appreciated that the teeth 27 of the toothed rack 26 may slide past the upper surface 122 when the detection link 42 is positioned within the detection link channel 124.

Figure 20:
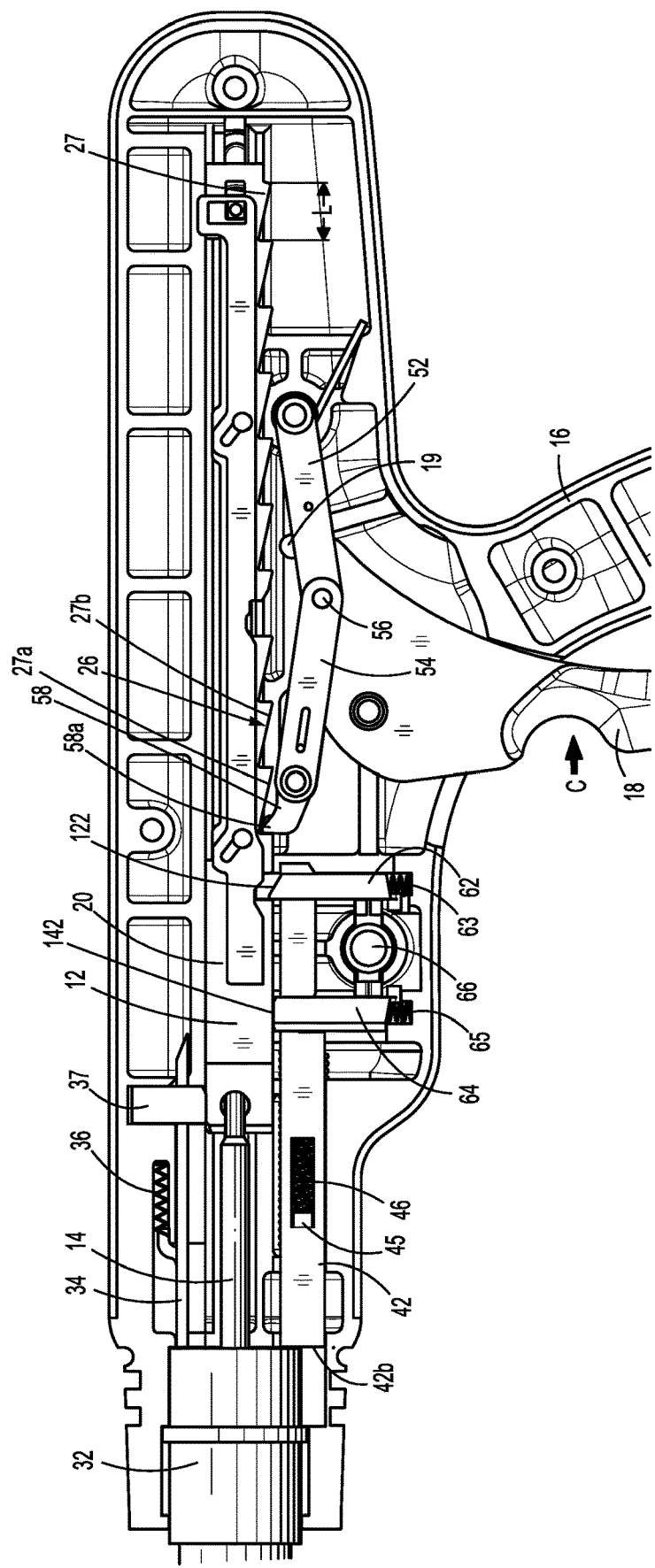
FIG. 20 is a side view of the universal handle of FIG. 18 with the moveable handle actuated.

Referring now to FIG. 20, with the circular loading unit 210 coupled to the handle 10, the moveable handle 18 is actuated such that the drive finger 19 of the moveable handle 18 engages the drive pin 56 to straighten the pairs of links 52, 54 and advance the drive pawl 58 into the teeth 27 of the actuation shaft 20 to advance the actuation shaft 20. With each actuation of the moveable handle 18 the drive pawl 58 advances the actuation shaft 20 a length L which is equal to the length L of one tooth 27 such that the drive finger 58a sequentially engages the teeth 27 as the moveable handle 18 is actuated. For example, during the first actuation of the moveable handle 18, the drive finger 58a engages a vertical surface of the actuation shaft 20 distal to the first tooth 27a and during the second actuation of the moveable handle 18, the drive finger 58a engages the proximal vertical surface of the first tooth 27a. It will be appreciated that as the actuation shaft 20 is advanced, the upper surface 142 of the circular fire lock pawl 64 and the upper surface 122 of the linear fire lock pawl 65 may engage the tapered surface of teeth 27 such that the actuation shaft 20 is allowed to advance and may engage the proximal vertical surface of teeth 27 to prevent the actuation shaft 20 from retracting a distance greater than the length L of one tooth 27 (i.e., one of the upper surfaces 122, 142 engage the proximal vertical surface of one of the teeth 27 to prevent retraction of the actuation shaft 20).

With reference to FIGS. 21 and 22, the moveable handle 18 is actuated until the upper surface 142 of the circular fire lock pawl 54 is received in the circular fire lock slot 25 defined along the toothed rack 26 of the actuation shaft 20 (i.e., the actuation shaft 20 is in the circular clamped position). When the upper surface 142 of the circular fire lock pawl 64 is received in the circular fire lock slot 25 to prevent inadvertent firing of the surgical instrument 100, i.e., the actuation shaft 20 is locked in a circular clamped position and prevented from longitudinal advancement or retraction. It will be appreciated that the upper surface 142 of the circular fire lock pawl 54 is sized such that the circular fire lock pawl 54 is prevented from being received within the linear fire lock slot 24.

Figure 23:
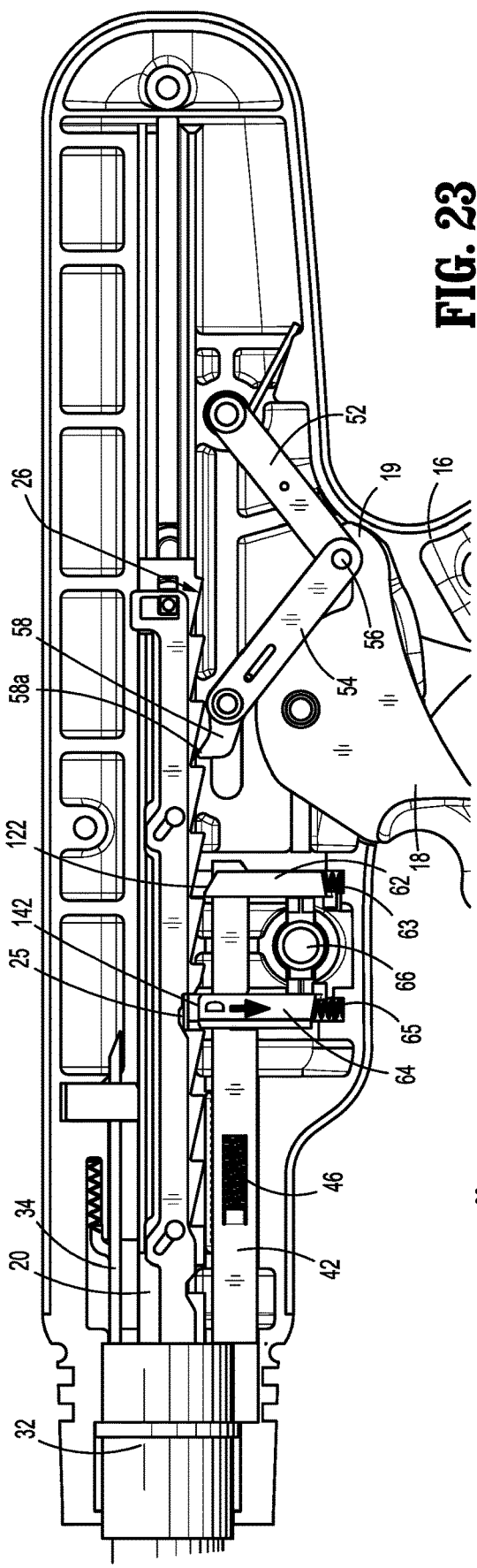
FIGS. 23 and 24 are a side view and a lower perspective view, respectively, of the universal handle of FIG. 21 with the fire button depressed.
Figure 24:
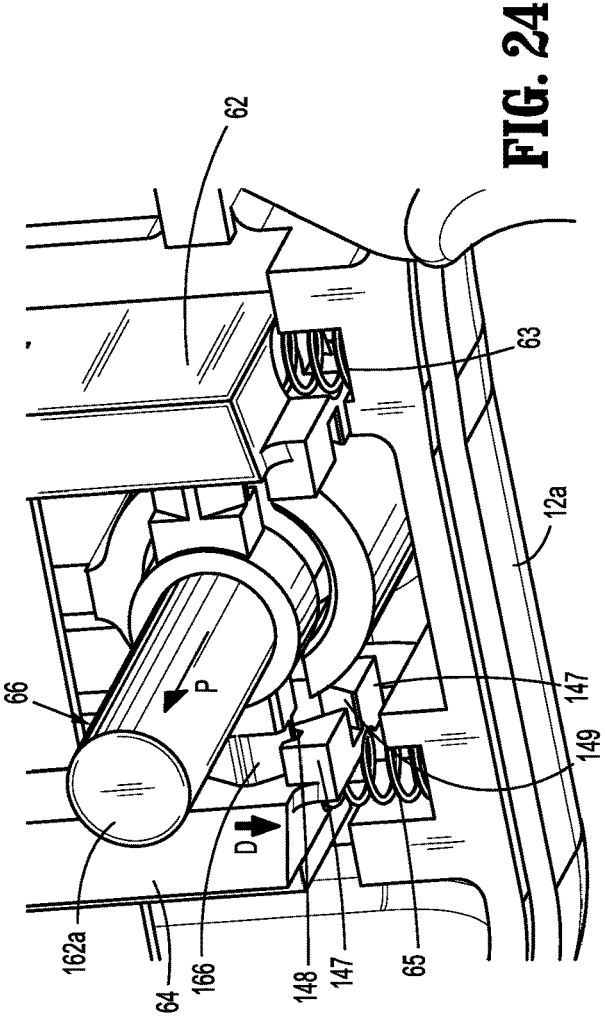

Referring to FIGS. 23 and 24, with the upper surface 142 of the circular fire lock pawl 54 received in the circular fire lock slot 25, the fire button 66 is depressed to move the fire button 66 from a rest or neutral position to a depressed position as shown by Arrow P. As the fire button 66 is depressed, the cam 166 of the fire button engages on of the camming protrusions 147 of the circular fire lock pawl 64 to move the circular fire lock pawl 64 downwardly away from the actuation shaft 20 such that the upper surface 142 of the circular fire lock pawl 64 is removed from the circular fire lock slot 25. When the fire button 66 is released in a depressed position, the cam 166 may be captured within a notch 148 defined in an upper surface of the camming protrusion 147 to retain the fire button 66 in the depressed position. It will be appreciated that the fire button 66 may be depressed in the direction represented by Arrow P or in a direction opposite the direction represented by Arrow P to permit right or left handed operation of handle 10.

With reference to FIG. 25, with the upper surface 142 of the circular fire lock pawl 64 removed from the circular fire lock slot 25, the handle 10 is actuated to advance the actuation shaft beyond the circular clamped position to fire the circular loading unit 210. The drive pawl 58 engages the toothed rack 26 to advance the actuation shaft 20. The geometry of the first and second links 52, 54 multiplies a handle force applied to the drive pin 56 by a force multiplier to a drive force applied to the toothed rack 26 of the actuation shaft 20. The handle force is the force applied to the drive pin 56 by the drive finger 19 and the drive force is the force applied to the toothed rack 26 by the drive finger 58a. The force multiplier may be in a range of about 1 to about 6 (e.g., 4). For example, the handle force may be 150 $lb_f$ and be multiplied a force multiplier of 4, determined by the geometry of the first and second links 52, 54, to a drive force of 600 $lb_f$.

It will be appreciated that during the second mode of operation, a single pull of the moveable handle 18 fires all the staples from a circular staple cartridge simultaneously.

In addition, similar to the first mode of operation, the teeth 27 of the toothed rack 26 are sized such that a full actuation of the moveable handle 18 advances the actuation shaft 20 the length L equal to the length of each tooth 27 to prevent half-firing of the handle 10 or cartridge 214 (FIG. 1).

Referring to FIG. 26, after the staples are fired or the tissue is to be released, the retraction knobs 71 (FIG. 1) are pulled to retract the actuation shaft 20 to the fully retracted position (FIG. 8) in a manner similar to the first mode of operation. As the retraction knobs 71 are pulled proximally, the coupling shaft 76 is moved proximally within the retraction slot 29 (FIG. 1) formed in the proximal end of the actuation shaft 20. As the coupling shaft 76 moves proximally in relation to the slide pins 72b and actuation shaft 20 such that pins 72b move within the release slots 72a of the release plate 72 to urge the release plate 72 downward. When the release plate 72 is moved downward, the release plate 72 moves below teeth 27 of the actuation shaft 20 and engages the drive finger 58a of the drive pawl 58 and the upper surface 142 of the circular fire lock pawl 64 to urge the drive pawl 58 and the circular fire lock pawl 64 out of engagement with the lower surface 23 of the actuation shaft 20 to facilitate retraction of the actuation shaft 20. The release plate 72 may also engage the upper surface 122 of the linear lock pawl 62 when the release plate 72 is moved below the lower surface 23 of the actuation shaft 20.

When the actuation shaft 20 is fully retracted and the loading unit 110, 210 is detached, the rack lock 37 is urged downwardly by the rack lock biasing member 39 into engagement with the distal end surface 21 of the actuation shaft 20 to lock the actuation shaft 20 in the fully retracted position. More specifically, when the loading unit 110, 210 is detached from the elongate member 13, the biasing member 36 urges the rack release member 34 distally to move the release finger 35 from the release slot 38 of the rack lock 37. When the release finger 35 is withdrawn from the release slot 38, the biasing member 39 urges the rack lock 37 downwardly to a position distal of the actuation shaft 20. When the actuation shaft 20 is in the fully retracted position, the fired staple cartridge 214 (FIG. 1) may be replaced with a new, fresh, unfired staple cartridge 114, 214 in the loading unit 110, 210, the entire loading unit 110, 210 may be replaced with a new, fresh, unfired loading unit 110, 210, or the handle 10 may be sterilized for reuse with another patient. Alternatively, the handle 10 may be disposable.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A universal surgical handle comprising:
   a body having a moveable handle, the movable handle transitionable from a home position to a first or second mode of operation;
   an elongate member extending distally from the body defining a longitudinal axis, the elongate member adapted to be coupled to a linear loading unit and to a circular loading unit;
   an actuation shaft defining a first lock slot and a second lock slot spaced axially from the first lock slot, the movable handle operatively associated with the actuation shaft to effect longitudinal movement of the actuation shaft; and
   a fire lock mechanism having at least one lock pawl, the at least one lock pawl received within the first lock slot in the first mode of operation of the handle to lock the actuation shaft in a first longitudinal position within the body and received within the second lock slot in the second mode of operation of the handle to lock the actuation shaft in a second longitudinal position different from the first longitudinal position within the body,
   wherein the handle transitions from the home position to the first mode of operation in response to a linear loading unit being coupled to the elongate member and transitions from the home position to the second mode of operation in response to a circular loading unit being coupled to the elongate member.

2. The handle according to claim 1, wherein the first loading unit type is a linear loading unit and the second loading unit type is a circular loading unit.

3. The handle according to claim 1, further comprising a drive rod extending through the elongate member and having a proximal end and a distal end, the proximal end of the drive rod being coupled to the distal end of the actuation shaft such that longitudinal movement of the actuation shaft effects longitudinal movement of the drive rod.

4. The handle according to claim 1, further comprising a detection link translatable between a first position and a second position proximal to the first position in response to a loading unit being coupled to the elongate member, the detection link configured to transition the handle between the first mode of operation when the detection link is in the first position and the second mode of operation when the detection link is in the second position.

5. The handle according to claim 4, wherein the at least one lock pawl includes a first lock pawl configured to lock the actuation shaft in the first longitudinal position during the first mode of operation and a second lock pawl configured to lock the actuation shaft in the second longitudinal position during the second mode of operation.

6. The handle according to claim 5, wherein the detection link is configured to prevent the second lock pawl from being received in the second lock slot during the first mode of operation.

7. The handle according to claim 6, wherein the second lock pawl defines a detection link passage that slidably receives the detection link, the detection link engaging a lower surface of a portion of the second lock pawl defining the detection link passage to prevent the second lock pawl from engaging the actuation shaft when the detection link is in the first position.

8. The handle according to claim 5, wherein the first lock pawl is receivable in the first lock slot of the actuation shaft during the first mode of operation to lock the actuation shaft in the first longitudinal position, the detection link being configured to prevent the first lock pawl from being received in the first lock slot during the second mode of operation.

9. The handle according to claim 8, wherein the first lock pawl defines a detection link channel that slidably receives the detection link, the detection link engaging a lower surface of a portion of the first lock pawl defining the detection link channel engaging the detection link to prevent the first lock pawl from engaging the actuation shaft when the detection link is in the second position.

10. The handle according to claim 8, wherein the detection link defines a locking recess in a lower surface thereof and the second lock pawl defines a detection link passage that slidably receives the detection link, the locking recess of the detection link positioned within the detection link passage of the second lock pawl when the detection link is in the second position such that the second lock pawl engages the actuation shaft.

11. The handle according to claim 5, wherein the fire lock mechanism includes a fire button positioned between the first and second lock pawls, the fire button depressible to move the first lock pawl out of engagement with the actuation shaft when the actuation shaft is in the first longitudinal position during the first mode of operation and the fire button depressible to move the second lock pawl out of engagement with the actuation shaft when the actuation shaft is in the second longitudinal position during the second mode of operation.

12. The handle according to claim 11, wherein the first lock pawl includes camming protrusions protruding distally from a distal face thereof that define a cam slot therebetween and the fire button includes a first cam protruding proximally that is positioned within the cam slot when the fire button is in a neutral position, the first cam of the fire button engaging one of the camming protrusions of the first lock pawl when the fire button is moved to a depressed position when the actuation shaft is in the first longitudinal position during the first mode of operation to remove the first lock pawl from first lock slot of the actuation shaft.

13. The handle according to claim 11, wherein the second lock pawl includes camming protrusions protruding proximally from a proximal face thereof that define a cam slot therebetween and the fire button includes a second cam protruding proximally that is positioned within the cam slot when the fire button is in a neutral position, the second cam of the fire button engaging one of the camming protrusions of the second lock pawl when the fire button is moved to a depressed position when the actuation shaft is in the second longitudinal position during the second mode of operation to remove the second locking pawl from the second lock slot of the actuation shaft.

14. The handle according to claim 1, further comprising a rack lock positioned distal to the actuation shaft when the handle is in the home position and the actuation shaft is in a fully retracted position proximal to the first and second longitudinal positions, the rack lock configured to engage the actuation shaft to prevent distal movement of the actuation shaft from the fully retracted position.

15. The handle according to claim 14, further comprising a rack release moveable in a direction parallel to the longitudinal axis to move the rack lock out of engagement with the actuation shaft.

16. A surgical instrument comprising:
a universal surgical handle including:
a body having a moveable handle;
an elongate member extending distally from the body defining a longitudinal axis;
an actuation shaft defining a first lock slot and a second lock slot spaced axially from the first lock slot, the movable handle operatively associated with the actuation shaft to effect longitudinal movement of the actuation shaft; and
a fire lock mechanism having at least one lock pawl, the at least one lock pawl received within the first lock slot during a first mode of operation of the handle to lock the actuation shaft in a first longitudinal position and received within the second lock slot during a second mode of operation of the handle to lock the actuation shaft in a second longitudinal position different from the first longitudinal position; and
a loading unit coupled to the elongate member, the universal surgical handle being transitioned to one of the first or second modes of operation in response to the loading unit being coupled to the elongate member, wherein the universal handle is transitioned to the first mode of operation when the loading unit is a linear loading unit and is transitioned to the second mode of operation when the loading unit is a circular loading unit.

17. The surgical instrument according to claim 16, wherein the universal surgical handle includes a plunger positioned about the longitudinal axis distal to the actuation shaft, the plunger translatable along the longitudinal axis, the first loading unit engaging the plunger when the loading unit is coupled to the handle to move the plunger towards the actuation shaft.

18. The surgical instrument according to claim 17, wherein the universal surgical handle includes a rack lock positioned distal to the actuation shaft when the actuation shaft is in a fully retracted position proximal to the first and second longitudinal positions, the rack lock being configured to lock the actuation shaft in the fully retracted position, the loading plunger configured to engage a rack release when the loading unit is coupled to the handle to move the rack lock to unlock the actuation shaft.

19. The surgical instrument according to claim 18, wherein when the loading unit is a first loading unit type, the plunger is moved from a home plunger position to a first plunger position wherein the plunger engages the rack release to move the rack lock to unlock the actuation shaft and the handle is in the first mode of operation, and wherein when the loading unit is a second loading unit type, the plunger is moved from the home plunger position to a second plunger position proximal to the first plunger position wherein the plunger engages the rack release to move the rack lock to unlock the actuation shaft and engages the detection link to transition the handle to the second mode of operation.

* * * * *